United States Patent
Dickie et al.

(10) Patent No.: US 11,983,842 B2
(45) Date of Patent: May 14, 2024

(54) METHOD AND SYSTEM FOR DISPLAYING AN ULTRASOUND IMAGE IN RESPONSE TO SCREEN SIZE

(71) Applicant: Clarius Mobile Health Corp., Vancouver (CA)

(72) Inventors: Kris Dickie, Vancouver (CA); Trevor Stephen Hansen, North Vancouver (CA); Benjamin Eric Kerby, Richmond (CA); Laurent Pelissier, North Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 51 days.

(21) Appl. No.: 17/959,281

(22) Filed: Oct. 3, 2022

(65) Prior Publication Data

US 2023/0031747 A1 Feb. 2, 2023

Related U.S. Application Data

(63) Continuation of application No. 17/409,734, filed on Aug. 23, 2021, now Pat. No. 11,461,873, and a continuation of application No. 16/799,801, filed on Feb. 24, 2020, now Pat. No. 11,100,606.

(51) Int. Cl.
*G06T 3/40* (2006.01)
*A61B 8/00* (2006.01)

(52) U.S. Cl.
CPC ............. *G06T 3/40* (2013.01); *A61B 8/465* (2013.01); *A61B 8/565* (2013.01)

(58) Field of Classification Search
CPC ........................................................ G06T 3/40
See application file for complete search history.

(56) References Cited

U.S. PATENT DOCUMENTS

| | | | |
|---|---|---|---|
| 7,457,656 B2 | 11/2008 | Judd et al. | |
| 9,269,323 B2 | 2/2016 | Edmiston et al. | |
| 9,972,111 B2 | 5/2018 | Eckert | |
| 11,100,606 B1 | 8/2021 | Dickie et al. | |
| 11,461,873 B2 | 10/2022 | Dickie et al. | |
| 2019/0059851 A1* | 2/2019 | Rothberg | A61B 8/42 |
| 2021/0041558 A1* | 2/2021 | Akkaraju | A61B 8/465 |
| 2021/0383503 A1 | 12/2021 | Dickie et al. | |

* cited by examiner

*Primary Examiner* — Shivang I Patel
(74) *Attorney, Agent, or Firm* — Julian Ho; Susan Ben-Oliel

(57) ABSTRACT

Ultrasound images are adjusted according to the size of the display area available to display them, so that image detail is displayed with a large enough physical size to discern comfortably. A translation ratio is determined for translating the physical distance traversed by the ultrasound signals of an ultrasound images to a corresponding physical distance on a screen of the display device. If the ratio is not below a threshold, the image is displayed in full. If the ratio is below the threshold, the image is cropped, optionally scaled, and displayed in the available area. Scaling and cropping may be based on window size and threshold window size. The parameters of the ultrasound scan may be controlled based on the scaling, cropping, or available screen size. User interface features may be displayed on the screen depending on how much area is available when the image is displayed.

21 Claims, 9 Drawing Sheets

METHOD AND SYSTEM FOR DISPLAYING AN ULTRASOUND IMAGE IN RESPONSE TO SCREEN SIZE

CROSS-REFERENCE TO RELATED APPLICATION

This application is a continuation of U.S. patent application Ser. No. 17/409,734 entitled "METHOD AND SYSTEM FOR DISPLAYING AN ULTRASOUND IMAGE IN RESPONSE TO SCREEN SIZE" filed Aug. 23, 2021, which is the continuation of U.S. patent application Ser. No. 16/799,801 entitled "METHOD AND SYSTEM FOR DISPLAYING AN ULTRASOUND IMAGE IN RESPONSE TO SCREEN SIZE" filed Feb. 24, 2020. The entire contents of both U.S. patent application Ser. No. 17/409,734 and U.S. patent application Ser. No. 16/799,801 are hereby incorporated by reference.

TECHNICAL FIELD

This disclosure relates to displaying ultrasound images. In particular, it relates to systems and methods for adapting the display of an ultrasound image to the size of an application window displayed on a screen.

BACKGROUND

Ultrasound is a useful, non-invasive imaging technique capable of producing real time images of internal structures within tissue. Ultrasound imaging has an advantage over X-ray imaging in that ultrasound imaging does not involve ionizing radiation.

Some mobile ultrasound scanners such as app-based ultrasound scanners require an add-on device with a screen that may act as both as a display and a control device. Examples of these add-on devices are mobile phones, tablets, laptops, and/or desktop computers. The screen size on these add-on devices can vary greatly. For example, the screen can sometimes be small (e.g., on a smartphone), which means that the displayed ultrasound image is correspondingly small and potentially difficult to read. On the other hand, the screen size can also be relatively large (e.g., on a tablet), such that if the ultrasound image is made to fit the larger screen, the ultrasound image may appear pixelated and also potentially difficult to read.

There is therefore a need for a way to display an ultrasound image that is suited to the size of the screen, and more particularly to the size of an application window displayed on the screen, such that the user does not need to manually scale the ultrasound image.

The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

A. Glossary

Figure 1:
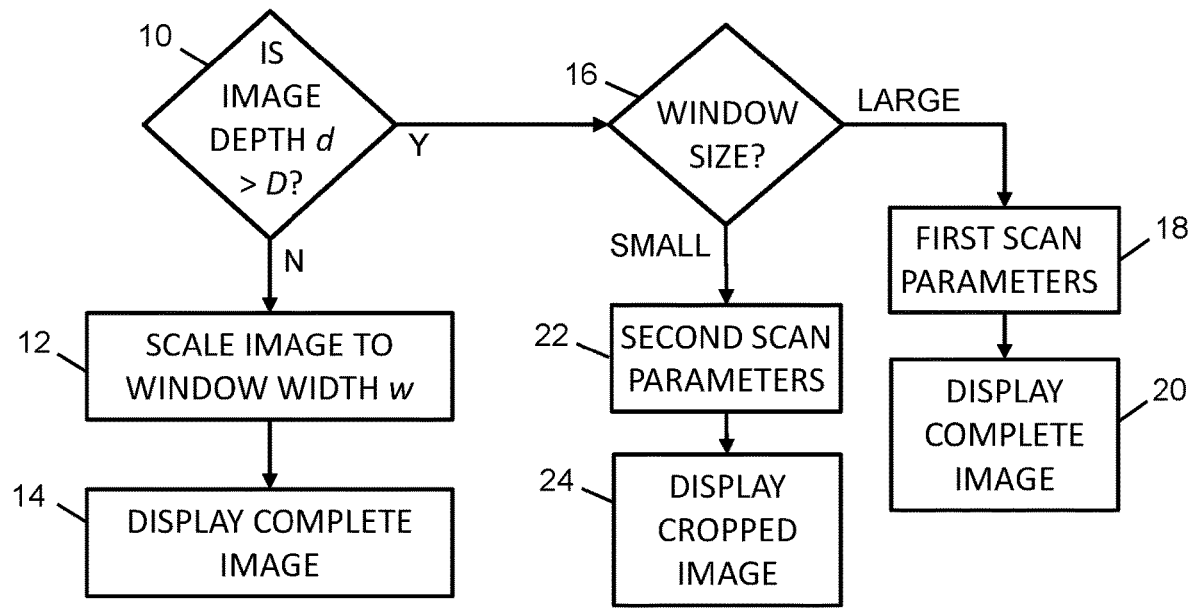
FIG. 1 is a flowchart representing a first process according to an embodiment of the present invention.

The term "application window" may refer to the area on a display screen that is available for displaying an ultrasound image by an application running on the device that hosts the screen.

The term "complete ultrasound image" refers to a full ultrasound image without any cropping, or in some cases with minor cosmetic cropping.

The term "depth" when relating to an ultrasound image refers to a measure of how far into the structure being scanned (e.g., tissue or a phantom) a given ultrasound image shows.

The term "module" can refer to any component in this invention and to any or all of the features of the invention without limitation. A module may be a software, firmware or hardware module, and may be located, for example, in the scanner or a display device.

The term "network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A network could also mean dedicated connections between computing devices and electronic components, such as buses for intra-chip communications.

The term "operator" may refer to the person that is operating an ultrasound scanner (e.g., a clinician, medical personnel, a sonographer, ultrasound student, ultrasonographer and/or ultrasound technician).

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by code or a module. The processor, if comprised of multiple processors, may be located together or geographically separate from each other. The term includes virtual processors and machine instances as in cloud computing or local virtualization, which are ultimately grounded in physical processors.

The term "scan conversion" refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for adapting display of an ultrasound image to a screen or in an application window displayed on the screen, the system being the subject of the present invention.

The term "ultrasound media" herein refers to an ultrasound video or a still ultrasound image. A frame of an ultrasound video may be referred to as a "still". An ultrasound video may be live or pre-recorded, or may be computer generated, e.g. for training purposes.

B. Exemplary Embodiments

Referring to FIG. 1, a first exemplary process is shown for displaying an ultrasound image (or any other ultrasound media) in an application window displayed on a screen, in which the way the ultrasound image is displayed depends on the size of the application window. In some examples, the display device in which the screen is present is only capable of displaying a single application window at a time, and hence the size and shape of the screen are the same as for the single application window. In other embodiments, the display device is capable of displaying multiple application windows at the same time, and hence the application window for the display of ultrasound images may be smaller than the size of the screen. In some cases, the application window may have a decorative border displayed around it or within it; in either of these cases the application window may be considered to be the area within the border.

In step 10, it is determined by the display device whether the depth d of the ultrasound image is greater than a threshold depth D. If the depth of the ultrasound image is less than the threshold depth D (the 'N' branch at step 10), then the ultrasound image may be scaled, in step 12, so that the width of the ultrasound image matches the width w of the application window. Then, in step 14, the complete ultrasound image may be displayed in the application window. Optionally, instead of scaling the width of the ultrasound image to match the full width w of the application window, the ultrasound image may be scaled so that its width is smaller than the width w of the application window.

In some embodiments, before displaying the complete ultrasound image, it may be cropped for cosmetic purposes while still generally maintaining substantially the full amount of image data available in the ultrasound image. If this cosmetic cropping occurs, the resulting image may still be referred to as a complete ultrasound image.

Referring still to FIG. 1, if the depth of the ultrasound image is greater than the threshold depth D (the 'Y' branch at step 10), then the display device may determine the size of the application window available for displaying the ultrasound image. The size of the application window may be represented by different criteria. For example, these criteria may include one or more of: a number of pixels along a long edge of the application window, a number of pixels along a short edge of the application window, a total number of pixels of the application window, an aspect ratio, an orientation, a physical length of the application window, a physical width of the application window, a physical area of the application window, and/or any other representation that directly or indirectly allows for determination of the size of the application window.

The size of the application window may be determined by determining a single parameter of the application window, and it may suffice to determine only the width or only the height of the window, for example. For example, a vertical dimension of the application window may be determined, when the application window is in a portrait orientation. If the aspect ratio of the application window is known, or within a certain tolerable range, then determination of the vertical dimension may be sufficient to determine the size of the application window.

Once the size of the application window is determined, it can be categorized as 'large' or 'small' for the purposes of the example embodiment of FIG. 1. The various criteria noted above to determine application window size can, either individually or in combination, be used in this categorization. In some embodiments, for a given criteria, there may be a threshold value which separates the large screen sizes from the small screen sizes. For example, if the criteria used for determining application window size is a physical length of the application window (e.g., a threshold length of the screen set between 15-25 cm), then a threshold length above a given length may be considered large and an application window size below the threshold length may be considered small.

In step 16, if it is determined that the size of the application window is large, then the ultrasound scanner may be instructed to acquire the ultrasound scan data using a first set of scanning parameters (step 18). This first set of parameters may be configured to generate an image that has extra detail that can be seen on the large application window size. In step 20, the complete ultrasound image may then be displayed in the large application window.

If, in step 16, it is determined that the size of the application window is small (e.g., that at least one of the criteria than define the size of the window is below a threshold value), then the ultrasound scanner may be configured to acquire the ultrasound scan data using a second set of scanning parameters (step 22). The second set of parameters may generally acquire images that have less detail, since a smaller application window size may have less ability to display the full amount of detail that can potentially be viewable on a large application window size. In step 24, a cropped ultrasound image may then be displayed in the application window.

As shown in the method of FIG. 1, different acts are taken to adjust for the size of the application window that the ultrasound image is being displayed in. For example, in one instance, a first set of scan parameters may be used for acquiring ultrasound images that are to be displayed on a large application window size (step 18), whereas a second set of scan parameters (different from the first set) may be used to acquire ultrasound images that are to be displayed on a small window size (step 22). In another instance, the complete ultrasound image is displayed on a large application window size, whereas a cropped image is displayed on a small application window size.

With respect to the different sets of scan parameters, since the ultrasound images may be displayed at different sizes on the different sized application windows, it may be more efficient to acquire less scan data for the ultrasound images to be displayed on the physically smaller application window. This is because the higher resolution scan data may not contribute to the viewable quality of the displayed ultrasound image on the smaller application window size, and would therefore be redundant.

As an example, the first set of scanning parameters (used in act 18) may include more scan lines and/or a higher frame rate than the second set of scanning parameters (used in act 22). Additionally or alternatively, the first set of scanning parameters (used in act 18) may involve passing the acquired ultrasound scan data through an enhanced smoothing filter, whereas the second set of scanning parameters (used in act 22) may involve passing the acquired ultrasound scan data through a regular smoothing filter. Additionally or alternatively, the first set of scanning parameters (used in act 18) may involve passing the acquired ultrasound scan data through an enhanced speckle reduction process, whereas the second set of scanning parameters (used in act 22) may involve passing the acquired ultrasound scan data through a regular speckle reduction process.

In a further example, the pixel sampling rate may additionally or alternatively be modified when switching between the first set of scan parameters and the second set of scan parameters. For example, the first set of scanning parameters (used in act 18) may involve a higher pixel sampling rate to cover the larger number of pixels along the axial direction on a larger application window size, whereas the second set of scanning parameters (used in act 22) may use a lower pixel sampling rate to cover the fewer number of pixels along the axial direction on a smaller application window size (presuming a larger screen has a corresponding higher pixel density). For example, if the pixel sampling rate is one hundred '100' samples per centimeter of imaged tissue in the first set of scan parameters, the pixel sampling rate may take fifty '50' samples per centimeter of imaged tissue in the second set of scan parameters (or another number that is proportionately smaller based on the proportionate reduction in the screen size).

Another reason to reduce the pixel sampling rate for a less pixel-dense screen is to avoid aliasing artifacts. For example, acquiring an image at a pixel sampling rate that would be used for a large (typically higher pixel density) screen and then downscaling the image may produce an image that has aliasing artifacts. However, acquiring an image at a lower pixel sampling rate, and then upscaling the image may produce an image that has fewer aliasing artifacts.

With respect to whether a complete ultrasound image or a cropped ultrasound image is displayed, a large application window size may have more physical display space to show the full breadth of the ultrasound signal data that is acquired (act 20 in FIG. 1). For example, in a sector or a curvilinear image, the complete ultrasound image may be generated from a number of radial ultrasound signal lines, and each of these lines may contain image data at the user-configured imaging depth. On a large application window size, there may be sufficient physical space to display imaging data at the user-configured imaging depth from every scanline—including the leftmost and rightmost radial ultrasound scanlines.

However, to display the same complete ultrasound image on a small application window, it would typically be necessary to scale the complete ultrasound image down considerably. This may be undesirable because details in the scaled-down image would be difficult to view. Instead, act 24 may display a cropped ultrasound image when it is determined that the application window is small. The cropping at act 24 may take different forms. In an example embodiment, one or both sides of the ultrasound image may be cropped and the height of the ultrasound image can be scaled so that it corresponds to the vertical dimension of the application window. In this situation, the full depth of the ultrasound image may be displayed in the central portion of the ultrasound image, but the leftmost and rightmost edges of the display may not be viewable. For a sector or a curvilinear image, this may mean that image data deeper into the tissue generated from the leftmost and/or rightmost transducer elements are not viewable. However, the loss of ability to view this data may be acceptable because typical ultrasound scanning technique focuses on the central portion of the probe, and the full depth of the image data acquired from the center portion transducer elements are viewable. Indeed, because certain portions (e.g., the left or right most portions of the image) of the ultrasound image are cropped away so as not to be viewable, the remaining viewable portion of the image can be scaled up so that the center portion of the image can appear larger on the small application window size. This, in turn, may make certain details in the center portion of the image more easily viewable on the small application window size.

Referring still to FIG. 1, it is notable that the complete ultrasound image may be displayed in both acts 14 and 20. While the display of the complete ultrasound image in act 20 is in response to a determination that an application window size is large, no such determination is made when the complete ultrasound image is displayed in act 14. Thus, in certain instances, when act 14 is performed to display the complete ultrasound image (e.g., without cropping), the complete ultrasound image may potentially be displayed on a small application window. However, this would only happen if the imaging depth is shallower than a certain threshold depth D. At these shallower depths (e.g., at 1-4 centimeters), the tissue volume scanned may be much smaller than when the amount of tissue volume is scanned at deeper depths. If images obtained at these shallower depths were cropped, the cropping may have a disproportionately large effect on the amount of remaining meaningful content that is viewable. As such, in the embodiment of FIG. 1, it may be desirable to show the complete ultrasound image without any cropping at depths less than a certain threshold D, even on a small application window size. For example, this may allow an operator to view the full width of the shallow ultrasound data they desired to see. In some embodiments the threshold depth D may configured to be between 1-10 centimeters.

In some embodiments, whether the complete ultrasound image is displayed in steps 14 and 20, or whether a cropped ultrasound image is displayed in step 24, the operator of the scanner may still optionally zoom in and out of the image displayed in the application window.

Figure 2:
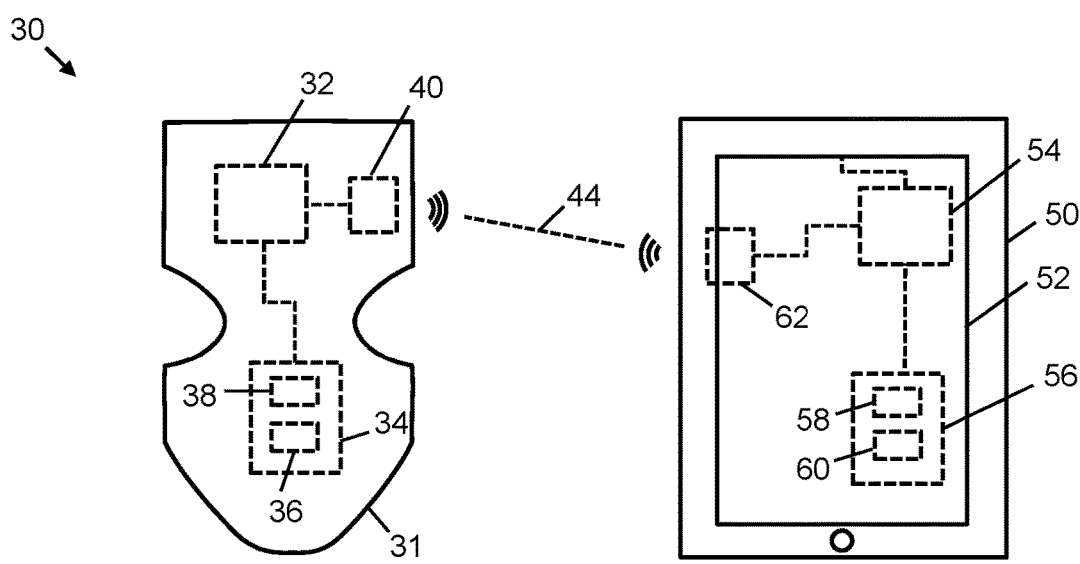
FIG. 2 is a schematic diagram of a system according to an embodiment of the present invention.

Referring to FIG. 2, an exemplary system 30 is shown for adapting display of an ultrasound image on a display device based on the size of the application window available for the display of the ultrasound image. The system 30 may include an ultrasound scanner 31 (hereinafter "scanner" for brevity) with a processor 32, which may be connected to a non-transitory computer readable memory 34 storing computer readable instructions 36 which, when executed by the processor 32, may cause the scanner 31 to provide one or more of the functions of the system 30. Such functions may include, for example, the acquisition of ultrasound data, the processing of ultrasound data, the transmission of ultrasound data to a display device 50, and the detection of operator inputs to the scanner 31.

The computer readable memory 34 may also store computer readable data 38. Computer readable data 38 may be used by the processor 32 in conjunction with the computer readable instructions 36 to provide the functions of the system 30. Computer readable data 38 may include, for example, configuration settings for the scanner 31, such as preset scan parameters that instruct the processor 32 how to collect and process the ultrasound data. Such a preset scan parameter may be selected, for example, depending on the size of the application window available on the screen 52 of the display device 50. In various embodiments, configuration settings may include any other data that is specific to the way that the scanner 31 operates.

The scanner 31 may include a communications module 40 connected to the processor 32. In the illustrated example embodiment, the communications module 40 may wirelessly transmit signals to and receives signals from the display device 50 along wireless communication link 44. The protocol used for communications between the scanner 31 and the display device 50 may be WiFi™ or Bluetooth™, for example, or any other suitable two-way radio communications protocol. The scanner 31 may operate as a WiFi™ hotspot, for example. Communication link 44 may use any suitable wireless network connection. While the illustrated example embodiment includes a wireless communication link 44 between the display device 50 and the scanner 31, in some embodiments, the connection between the scanner 31 and the display device 50 may be wired (e.g., via a USB-C, lightning, or other wired connection).

The display device 50 may be, for example, a laptop computer, a tablet computer, a desktop computer, a smart phone, a smart watch, smart glasses (e.g., spectacles with a built-in display), a television, a bespoke display or any other display device that is capable of being connected to the scanner 31. The display device 50 may host a screen 52 and include a processor 54. The processor 54 may be connected to a non-transitory computer readable memory 56 storing computer readable instructions 58 which, when executed by the processor 54, cause the display device 50 to provide one or more of the functions of the system 30. Such functions may be, for example, the receiving of ultrasound data that may or may not be pre-processed, scan conversion of ultrasound data that is received into an ultrasound media, the control of the scanner 31 via user input received at the display device 50, the display of an ultrasound image on the screen 52 (e.g., within an application window on the screen 52), and the adapting of the displayed ultrasound image for suitable display within the application window as described herein.

The computer readable memory 56 may also store computer readable data 60 which may be used by the processor 54 in conjunction with computer readable instructions 58 to provide the functions of the system 30. Computer readable data 60 may include, for example, settings for the scanner 31, such as preset scan parameters for acquiring ultrasound data depending on the size of the screen 52 or application window on the screen 52, and/or settings for a user interface displayed on the screen 52. Settings may also include any other data that is specific to the way that the scanner 31 operates or that the display device 50 operates.

It can therefore be understood that the computer readable instructions and data used for controlling the system 30 may be located either in the computer readable memory 34 of the scanner 31, the computer readable memory 56 of the display device 50, and/or both the computer readable memories 34, 56.

The display device 50 may also include a communications module 62 connected to the processor 54. In the illustrated example embodiment, the communications module 62 wirelessly transmits signals to and receives signals from the scanner 31 on wireless communication link 44. However, as noted, the communication link between display device 50 and the scanner 31 may be wired in some embodiments.

Referring still to FIG. 2, it is notable that different types of display devices 50 may have different sized screens 52. Generally, the embodiments described herein relate to methods of adapting the display of an ultrasound image to screens of different sizes.

Figure 3:
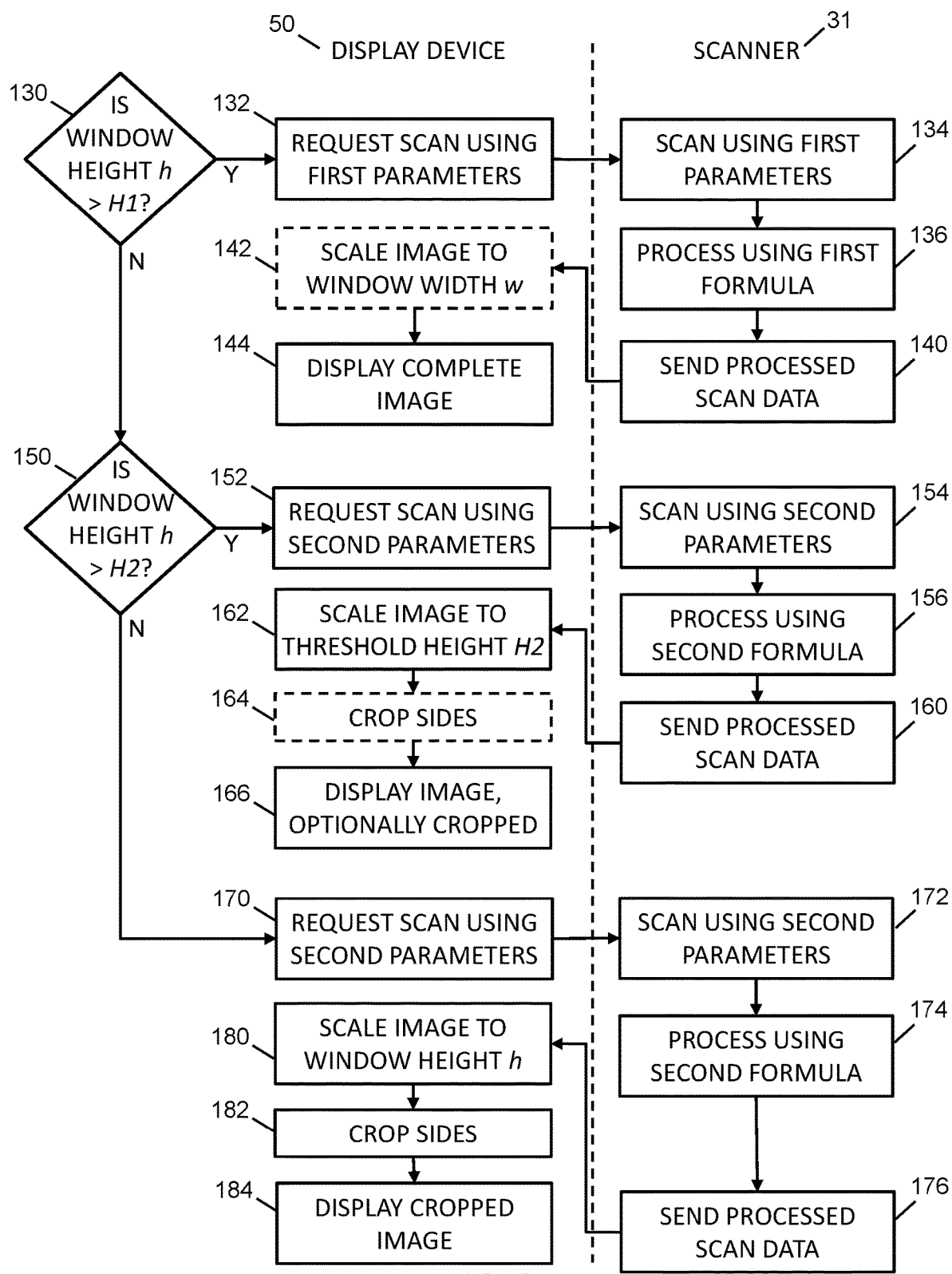
FIG. 3 is a flowchart representing a second process according to an embodiment of the present invention.

Referring to FIG. 3, shown there is a process performed by the system 30 for determining how to acquire and display an ultrasound image based on the characteristics of the application window, according to another embodiment. In describing the method of FIG. 3, reference will simultaneously be made to FIGS. 4-8, which show example display devices of various sizes. These various example display devices will be identified using the reference numerals 50a, 50b, 50c, 50d, and 50e; and their corresponding different-sized screens will be identified using 52a, 52b, 52c, 52d, and 52e respectively. The discussions below relate generally to example scenarios where the size of the screen 52 varies, and situations where the application window fills the entirety of the screens 52; however, analogous discussions are also applicable to application windows that only fill a portion of the screen 52.

In step 130, the system 30 may determine whether the application window, when in the portrait mode, has a height h (e.g., vertical dimension) that is greater than a threshold height H1. The height may be determined directly, for example, by determining a physical dimension in millimeters. For example, the physical dimension in millimeters of a screen may be can value that can be determined from an operating system (e.g., either iOS™ or Android™ operating systems) application programming interface (API). Additionally or alternately, the height h may be determined indirectly, for example by determining the number of pixels, the width of the application window, or any other indicator of the size of the application window, and then translating that indicator into the height of the physical height of the application window.

If the height of the application window is greater than the threshold H1 (the 'Y' branch of act 130) then, in step 132, the display device 50 may request the scanner 31 to acquire the ultrasound data using a first set of scan parameters. Similar to the first set of scan parameters discussed in relation to FIG. 1 above that are used to acquire ultrasound image data for the large application window size, the first set of scan parameters here are configured to be sufficiently robust to generate an ultrasound image that is suitable for display a relatively large application window size. For example, the first set of scan parameters may have a relatively high frame rate (e.g., to reduce potential flicker of the ultrasound image feed) and/or a relatively high number of scan lines (e.g., to reduce the likelihood of the ultrasound image feed appearing pixelated).

In response, in step 134, the scanner may perform the scan using the first set of parameters. In some embodiments, the first set of parameters may include a first formula or an indication of a first formula with which to process the scan data. For example, the formula may be a formula for smoothing the scan data and/or reducing speckle. In step 136, the scanner 31 may process the scan data with the first formula. In step 140, the scanner 31 may then send the processed scan data to the display device 50.

In step 142, the display device 50 may optionally scale the ultrasound image so that its width is equal to the width w of the application window. In step 144, the display device 50 may then display the complete ultrasound image in the application window. The displayed ultrasound image may correspond, for example, to the complete ultrasound image 76 displayed on the large screen 52a of FIG. 4.

Figure 4:
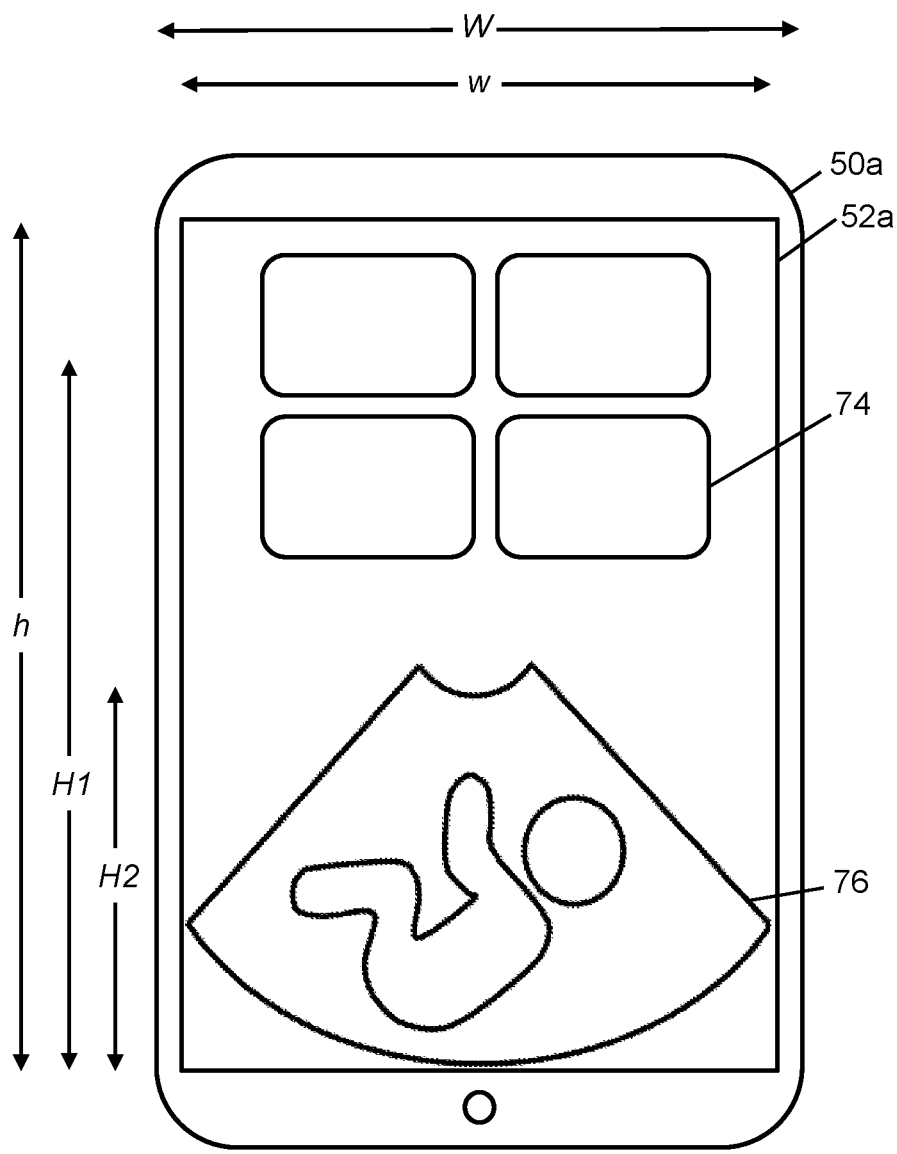
FIGS. 4-8 are schematic diagrams of a display device with varying screen sizes displaying an ultrasound image, according to various embodiments of the present invention.

Referring simultaneously to FIG. 4, a display device 50a with screen 52a is shown. The screen 52a may be considered to be large because it has a vertical dimension h that is greater than the threshold dimension H1. Pursuant to act 144 in the method of FIG. 3, the ultrasound image 76 may thus be displayed as a complete ultrasound image. Also, pursuant to act 142 in the method of FIG. 3, the complete ultrasound image 76 is scaled so that its width is equal to the width w of the screen 52a.

Since the screen 52a is larger than height threshold H1, it is likely a relatively tall display. As such, even after scaling the ultrasound image so that it fits the width of the screen 52a, there may be residual vertical blank space (either above or below) the ultrasound image 76. As shown in FIG. 4, the application window on the screen 52a may thus also contain user interface buttons 74 with the ultrasound image 76. The user interface buttons may, for example, be for freezing the ultrasound image 76, changing the mode of operation of the scanner 31, adjusting the gain of the scanner 31, and/or adjusting the depth of the ultrasound image 76.

In the discussion above, it was noted that act 142 in the method of FIG. 3 is optional so that the ultrasound image may not necessarily be scaled to the window width w. This is because for screens that are considerably larger than the screen 52a, scaling the image to fit the window width w may result in an ultrasound image that appears overly stretched and/or pixelated. Thus, in certain instances, this scaling may not be performed. Instead, the system 30 may be configured so that when the screen width is greater than the threshold width W, the width of the complete ultrasound image is scaled to the threshold width W and no wider. This threshold width may be determined in a manner that allows for sufficient detail of the ultrasound image to be readily discerned by an operator, but not so wide that it becomes the ultrasound image 76 would appear pixelated. For example, in various embodiments, the threshold width W may be between 20-25 centimeters.

Referring back to FIG. 3, if the height of the application window as determined in step 130 is not greater than the threshold height H1 (the 'N' branch of act 130), then the system 30 may determine whether the height of the application window is above a height threshold H2 that is smaller than H1 (act 150). If the height of the application window is greater than H2 (the 'Y' branch of act 150), then, in step 152 the display device 50 may request the scanner 31 to acquire the ultrasound image data using a second set of scan parameters. As discussed above in relation to FIG. 1 when ultrasound images are acquired for small application window sizes, this second set of scan parameters may have a lower density of ultrasound image data so as to avoid expending resources on acquiring and/or processing ultrasound image data that may have not have a visibly discernible difference on the ultrasound images when they are displayed on this intermediate-sized display that has a height in between H1 and H2. In various embodiments, this second set of scan parameters may have a lower frame rate and/or a lower number of scan lines relative to the first set of scan parameters used in act 134.

At act 154, the scanner 31 may perform the scan using the second set of parameters. In various embodiments, the second set of parameters may include a second formula or an indication of a second formula with which to process the scan data. For example, this may be a formula for smoothing the scan data or reducing speckle. In some embodiments, this second formula may be different from the first formula used in act 136. In some embodiments, the second formula may be the same formula used in the act 136, but parameterized differently to account for the smaller application window size. For example, the smoothing filter and/or the speckle reduction algorithm may be configured to operate in a coarser way since the more granular smoothing and/or speckle reduction operations may not be viewable on the smaller screen. At act 156, the scanner 31 may proceed to process the scan data with the second formula. At act 160, the scanner 31 may then send the processed scan data to the display device 50.

At step 162, the display device 50 may scale the ultrasound image so that its height is equal to the threshold height H2. Notably, this may happen for all application window heights that are generally in between the height thresholds H1 and H2. In effect, the threshold H2 becomes a maximize vertical height for how an ultrasound image would be displayed.

At step 164, the display device 50 may then optionally crop one or both of the left and right sides of the ultrasound image so that it fits in the application window. For some application window sizes and ultrasound image sizes, the sides of the ultrasound image may not need to be cropped, and hence step 164 is optional as it may not be performed. In step 166, the display device 50 may then display the ultrasound image, which may be cropped, in the application window.

Figure 5:
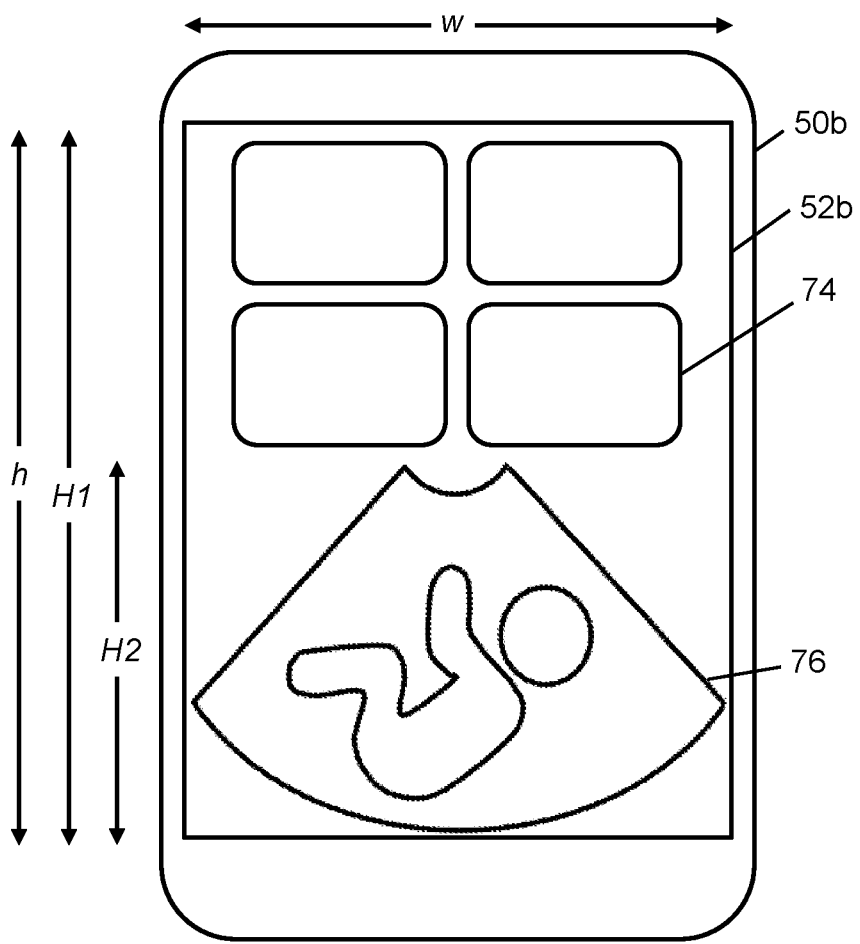
Figure 6:
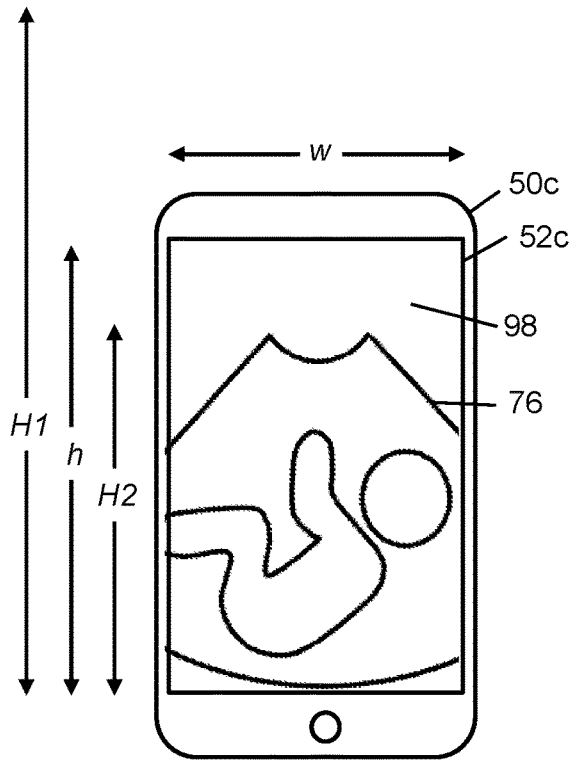

FIGS. 5 and 6 show two different example situations where the height h of the application window falls between H1 and H2. FIGS. 5 and 6 are discussed below in relation to the 'Y' branch of act 150 in FIG. 3.

Referring simultaneously to FIGS. 3 and 5, a display device 50b with an application window that fills screen 52b is shown. The screen 52b has a vertical dimension h that is equal to the threshold dimension H1. As such, the height h of screen 52b would not be considered greater than threshold H1 at act 130, but it would be considered greater than threshold H2 of FIG. 3 so as to trigger the 'Y' branch at act 150. On this screen 52b, the ultrasound image 76 may then be scaled vertically so that it matches the threshold height H2 at act 162. In the illustrated embodiment, since the screen 52b is wide enough to fit the full width of the ultrasound image 76, the optional cropping of act 164 need not be performed prior to the display of the ultrasound image at act 166. In the example embodiment of FIG. 5, the ultrasound image scaled to the maximum vertical threshold H2. Since the height h of the screen 52b is still higher than H2, the screen is still large enough to also display and a set of user interface buttons 74.

Referring now simultaneously to FIGS. 3 and 6, a display device 50c with an application window that fills screen 52c is shown. The screen 52c has an intermediate vertical dimension h that is below the threshold dimension H1 and greater than the threshold dimension H2 so that when the method of FIG. 3 is executed, the 'Y' branch of act 152 would be triggered. On the screen 52c, the height of the ultrasound image 76 is scaled to equal the threshold height H2 at act 162. However, in this embodiment, the width w of the screen 52*c* is not wide enough to fit the full width of the ultrasound image 76 after it has been scaled to the height threshold H2. As such, the left and right sides of the ultrasound image 76 are cropped at act 164 prior it is displayed at act 166.

By cropping the sides of the ultrasound image, the image is effectively zoomed-in in the more important detail in the center of the image 76. This makes the center portion of the ultrasound image 76 more comfortably visible to the operator of the scanner 31 than would be if the complete ultrasound image were to be displayed on the same screen 52*c* in the same portrait orientation (in which case, the same detail in the center portion of the ultrasound image 76 would appear smaller). The screen 52*c* may not be large enough to display both the ultrasound image 76 and a set of user interface buttons such as those on screen 52*a* and 52*b* shown on FIGS. 4 and 5 respectively. In the illustrated example, no user interface controls are shown in the available area 98. However, in some embodiments, the user interface controls 74 of FIGS. 4 and 5 could be made smaller in appearance. While this may potentially make the controls 74 more difficult to use, it will allow the user interface controls 74 to be retained and still be accessed.

Referring back to FIG. 3, if the height of the application window as determined in step 150 is not greater than the threshold height H2 (the 'N' branch of act 150), then, in step 170 the display device 50 may request the scanner 31 to acquire the ultrasound data using the second set of parameters. As illustrated, the same second set of scan parameters as is used in the 'Y' branch of act 150 is used as in the 'N' branch. This may facilitate ease of implementation so that there are only two set of scan parameters: e.g., for large and small application window sizes (e.g., when the application window height is above and below height threshold H1 respectively).

However, in some embodiments, act 170 may involve scanning with a third set of scan parameters that have even lower information density than the second set of scan parameters. Since the screen height in the 'N' branch of act 150 is even shorter than the height threshold H2, such potential third set of scan parameters can be further optimized to further reduce the acquired information since the acquired information will be even more difficult to view on the even smaller application window size that is less than height threshold H2. For example, this third set of scan parameters may have even fewer scan lines and/or a an even lower pixel sampling rate than the second set of scan parameters.

At act 172, the scanner 31 may perform the scan using the set of scan parameters that the display device 50 instructed it to use. In step 174, the scanner 31 may proceed to process the scan data with a formula. As illustrated in FIG. 3, this is the same second formula used in act 156 (e.g., the same configuration of the first formula used in act 136, as noted above). However, in some embodiments, this may be a third formula, or the same formula used in act 136 but parameterized in a third way to account for the even smaller application window size. For example, the smoothing filter and/or the speckle reduction algorithm may be configured to operate in a way that is even coarser, since finer smoothing or speckle reduction may not be viewable on the smaller screen. The scanner 31 may then send the processed scan data to the display device 50 (act 176).

In step 180, the display device 50 may scale the ultrasound image so that its height is equal to the height h of the application window. In this instance, since the application window height h not greater than the lower height threshold H2, it is likely that that the application window is quite small. As such, to maximize viewing of the ultrasound image on the relatively small screen, the ultrasound image can be scaled so that its height matches the height of the window.

Since the vertical dimension h of the application window is small, in portrait mode, it is likely the width of the application window is also small. Scaling the ultrasound image height to match the window height h may then result in the entire width of the ultrasound image not fitting into the available width of the application window for displaying the ultrasound image.

In step 182, the display device 50 may then crop one or both of the left and right sides of the ultrasound image so that a center portion of the ultrasound image can be viewable in the application window while its full height has been scaled to match the application window height h. The display device 50 may then display the cropped ultrasound image in the application window.

Figure 7:
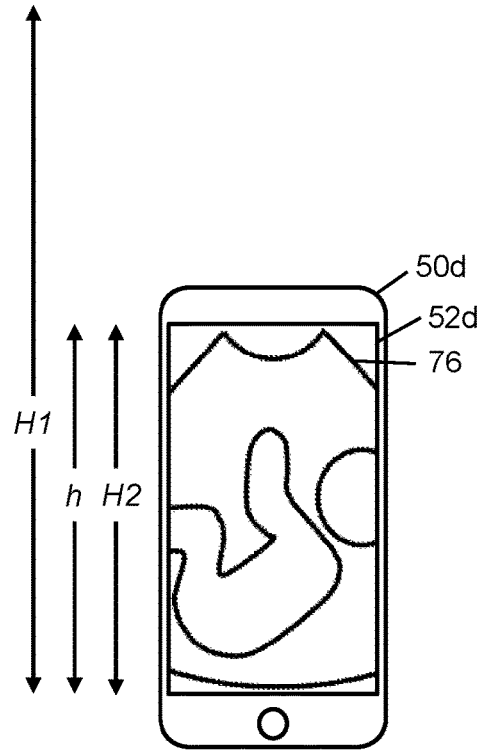
Figure 8:
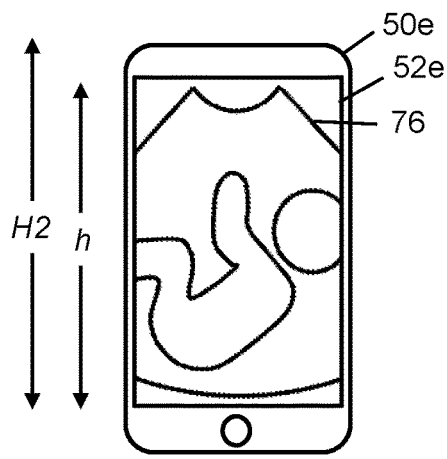

FIGS. 7 and 8 show two different example situations where the height h of the application window is not greater than threshold H2. FIGS. 7 and 8 are discussed below in relation to the 'N' branch of act 150 in FIG. 3.

Referring simultaneously to FIGS. 3 and 7, a display device 50*d* with an application window that fills screen 52*d* is shown. The screen 52*d* has a vertical dimension h that is equal to the threshold dimension H2. As such, the height h of screen 52*d* would not be considered greater than threshold H2 at act 150, and the 'N' branch at act 150 would be triggered. On this screen 52*d*, the ultrasound image 76 may then be scaled vertically so that it matches the application window height h at act 180. In the illustrated embodiment, scaling the image to fit the height h of the application window on screen 52*d* means the full width of the ultrasound image 76 cannot fit the screen 52*d*. Thus, at act 182, the ultrasound image 76 may be cropped. By cropping the sides of the ultrasound image, the image is effectively zoomed in on the center portion of the ultrasound image, which typically shows the more important detail desired to be viewed by the operator. The cropping thus allows this portion of the ultrasound image to be more comfortably visible to the operator of the scanner 31 than would be if the full width of the complete ultrasound image were to be displayed on the same screen 52*d* in the same portrait orientation.

Notably, scaling the ultrasound image 76 to the full height h of the screen 52*d* maximizes viewability of the ultrasound image 76 on the relatively small screen 52*d*, but it may also not leave room to display any of the user interface controls such as those that appear on screens 52*a* and 52*b* shown in FIGS. 4 and 5 respectively. Thus, in these embodiments, the user input that would have been received via those user interface controls may instead be accessible by double-tapping on the screen 52*d*, for example, where the screen 52*d* is a touchscreen; or via input (e.g., buttons) available on the scanner 31 itself.

Referring now simultaneously to FIGS. 3 and 8, a display device 50*e* with an application window that fills screen 52*e* is shown. The screen 52*e* has a small vertical dimension h that is below the threshold dimension H2, so that the 'N' branch at act 150 would be triggered. Thus, similar to the embodiment of FIG. 7, the height of the ultrasound image 76 is scaled to equal the threshold height h of the application window at act 180. Also similar to the embodiment of FIG. 7, scaling the image to fit the height h of the application window on screen 52*e* means the full width of the ultrasound image 76 cannot fit the screen 52*e*. Thus, at act 182, the sides of the ultrasound image 76 may be similarly cropped so that the center portion of the ultrasound image can be more easily viewed by the operator. Since the screen 52e is even smaller that the screen 52d, there is the same lack of space for displaying user interface controls as was the case for the example of FIG. 7. As such, user interface input may be provided in the alternate ways noted above.

Considering the various example application window sizes shown in FIGS. 4-8 together, the method of FIG. 3 can be considered a way of optimizing quality of the displayed ultrasound image with respect to application window size (and in certain cases, screen size). As the application window size is reduced in size from screen 52a (FIG. 4) to screen 52b (FIG. 5), the scale of the ultrasound image is reduced accordingly, with its width being scaled to the width w of the screen. As the screen is further reduced in size from screen 52b to screen 52c (FIG. 6), the scale of the ultrasound image 76 can remain the same, with an image height equal to H2, but its sides become increasingly cropped. As the screen is again reduced in size from screen 52c to screen 52d (FIG. 7), the scale of the ultrasound image 76 can again remain the same, with an image height equal to H2, but the sides of the image are further cropped. As the screen is even further reduced in size from screen 52d to screen 52e (FIG. 8), the scale of the ultrasound image can be further reduced so as to retain the full height of the image displayed on the screen, and also so as not to crop too much of the more important detail that is found in the center of the ultrasound image.

Figure 9:
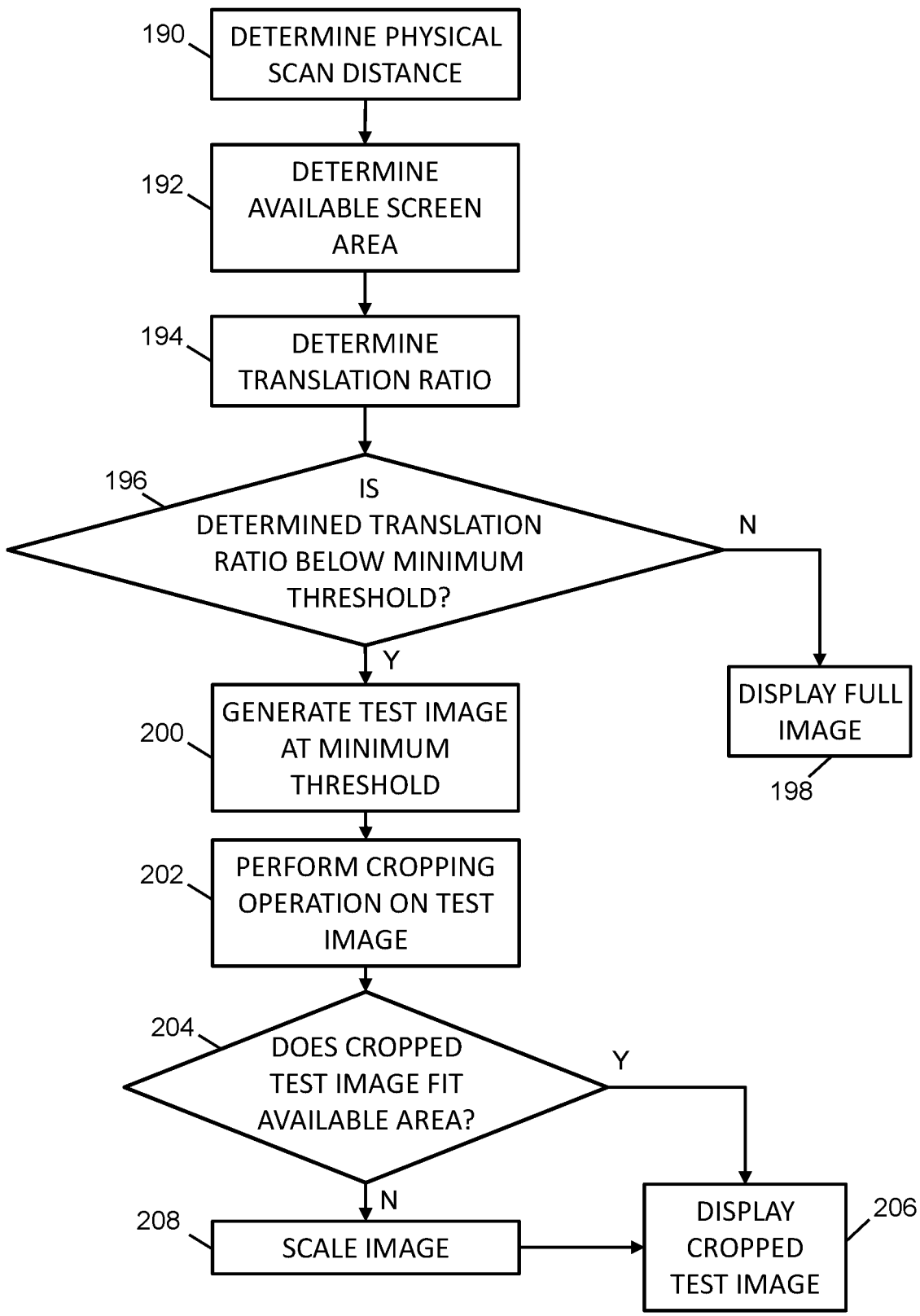
FIG. 9 is a flowchart representing a third process according to an embodiment of the present invention.

Referring to FIG. 9, shown there is a method of adapting display of an ultrasound image on a display device, according to another embodiment of the present disclosure. In step 190, a physical scan distance is determined. This distance can be any distance traversed by an ultrasound signal to generate the ultrasound image. For example, it can be the full depth of an ultrasound scan or any portion thereof. Note that the ultrasound signals may traverse a physical distance twice (e.g., once in each direction), and it is the measure of the physical distance that is determined rather than the total round-trip path of the ultrasound signals.

In step 192, the available screen area may be determined, including the dimensions of the available screen area. This information may be determined from available operating system API calls, in a manner similar to how the height h is determined with respect to the method of FIG. 3 above.

In step 194, a translation ratio is determined. The translation ratio may be an indication of the physical size of the ultrasound image (were it to be displayed) in comparison to the actual physical depth of the ultrasound scan. To determine the translation ratio, it would first be determined what the size of the ultrasound image would be were it to be displayed as a complete ultrasound image on the available area of the screen (e.g., the complete ultrasound image would be fitted to the available display area). Then, a physical distance on that displayed ultrasound image would be divided by the corresponding physical distance traversed by the ultrasound signal. For example, on a given screen, 1 cm on a complete ultrasound image (when fitted to the display) may correspond to 2 cm of imaged tissue. This would then provide a translation ratio of 0.5, for example.

In step 196, the determined translation ratio is compared to a minimum threshold translation ratio. If the determined translation ratio is not below the minimum threshold translation ratio (the 'N' branch at act 196), the appearance of imaged structures on the screen may be considered large enough, and the ultrasound image may be displayed in full in step 198. If, however, the determined translation ratio is below the minimum threshold translation ratio (the 'Y' branch at act 196), the appearance of imaged structures on the screen may be considered too small for the detail of those structures to be seen clearly by an operator of the ultrasound scanner. In this case, the ultrasound image may need to be further processed so that such detail may appear at a greater magnification. In various embodiments, the minimum threshold ratio may be between 0.25-1.

In step 200, a test ultrasound image may be created at the minimum threshold translation ratio. That is, a test ultrasound image may be created which has a size that, if displayed, would have a translation ratio that is equal to the minimum threshold translation ratio. In step 202, a cropping operation may be performed on the test ultrasound image. In various embodiments, the cropping operation may involve the removal of: one or both sides of the test ultrasound image by a predefined number of pixels or a predefined percentage of the width of the test ultrasound image; a top of the test ultrasound image by a predefined number of pixels or a predefined percentage of the height of the test ultrasound image; a bottom of the test ultrasound image by a predefined number of pixels or a predefined percentage of the height of the test ultrasound image; a combination of two or more of the foregoing; or using any other suitable rule.

In some embodiments, the cropping operation may involve cropping the test ultrasound image at various crop ratios (a crop ratio being a ratio of the area of the post-cropped image relative to the pre-cropped image), and testing whether a cropping a given crop ratio results in an image that fits the available area of the screen. For example, in some embodiments, after cropping the test ultrasound image at a first crop ratio, the cropped image can be tested to determine if it fits the available physical area of the screen. If so, it can be displayed without scaling. If not, the test ultrasound image can be further cropped at a second crop ratio, and that cropped image can be tested to determine if it fits the available physical area of the screen. If so, the test ultrasound image cropped at the second crop ratio can be displayed in the available physical area of the screen. If not, the test ultrasound image cropped at the second crop ratio can be returned from the cropping operation for the determination made at act 204.

Additionally or alternatively, the cropping operation may repeat a number of acts for successively smaller crop ratios. For example, the cropping operation may involve repeatedly: cropping the test ultrasound image at a test crop ratio, determining whether the test ultrasound image cropped at the test crop ratio fits the available physical area of the screen of the display device for displaying the ultrasound image, and if the test ultrasound image cropped at the test crop ratio fits the available physical area of the screen of the display device for displaying the ultrasound image, displaying the test ultrasound image cropped at the test crop ratio in the available physical area of the screen of the display device. These successive operations may be performed until a crop ratio limit is met. If the test ultrasound image cropped at the crop ratio limit does not fit the available physical area of the screen of the display device, the test ultrasound image cropped at the crop ratio limit may be provided as the cropped test ultrasound image generated from the cropping operation, and used for the determination made at act 204.

The crop ratio limit may be considered the minimum crop ratio that may be permitted before it can be considered that too much of the imaged tissue has been removed from the ultrasound image. Having a crop ratio limit may prevent overcropping an image to the point where what remains is no longer relevant for the operator to view. Examples of the crop ratio limit may vary for different types of ultrasound images, and are discussed with respect to the examples below.

Referring still to FIG. 9, at step 204, it is determined whether the cropped test ultrasound image fits within the available area of the screen in the current orientation of the screen. If the cropped test ultrasound image fits within the available area of the screen (the 'Y' branch of step 204), then, in step 206, the cropped test ultrasound image may be displayed. Notably, the cropped test ultrasound image would have a translation ratio that is at the minimum threshold translation ratio, which is larger than that the translation ratio would have been had the image been fitted to display the complete ultrasound image. While certain aspects of the image have been cropped, this allows the remaining visible portion of the ultrasound image (usually a center portion of the image) to appear larger in a manner that allows details within the imaged tissue to be more easily discernible to the operator.

If the cropped test ultrasound image does not within the available area of the screen (the 'N' branch at act 204), then, in step 208, the cropped test ultrasound image may be scaled to reduce it in size until it fits within the available area of the screen. After scaling, the scaled and cropped test ultrasound image may then be displayed in step 206.

Scaling the cropped test ultrasound image may involve scaling the cropped test ultrasound image generated from the cropping operation so that a vertical dimension of the scaled and cropped test ultrasound image substantially matches a vertical dimension of the available physical area of the display of the display device. When scaling the cropped test ultrasound image, the aspect ratio of the scaled and cropped test ultrasound image may be maintained the same as the aspect ratio of the ultrasound image.

As noted, in some embodiments, steps in FIG. 9 may be repeated. For example, the cropping may be done in one or more stages, with the cropped test image at each stage being tested to determine whether it fits within the available screen area.

Figure 10:
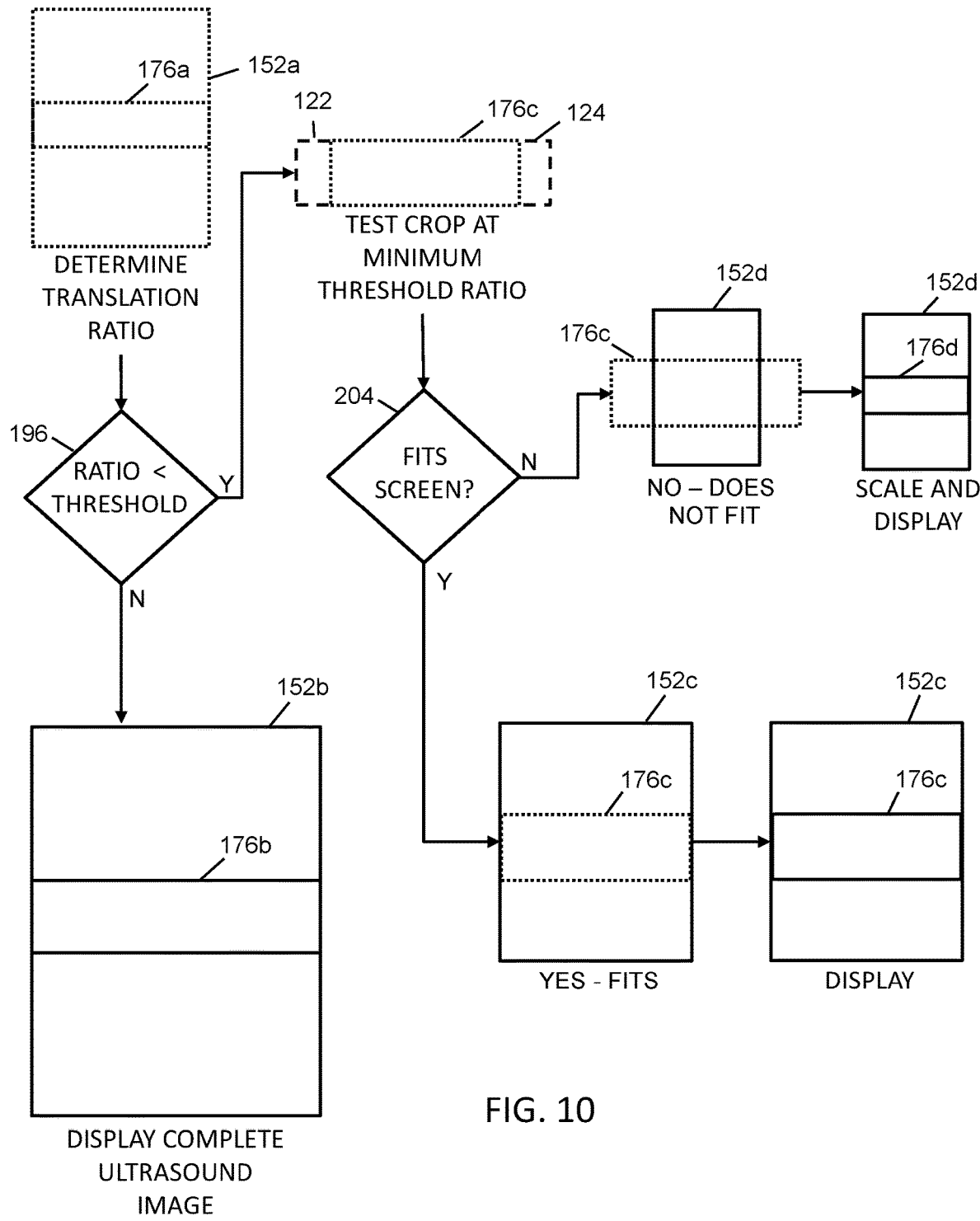
FIG. 10 is a schematic diagram illustrating the various steps in the third process when displaying a shallow ultrasound image on a screen in the portrait orientation, according to an embodiment of the present invention.
Figure 11:
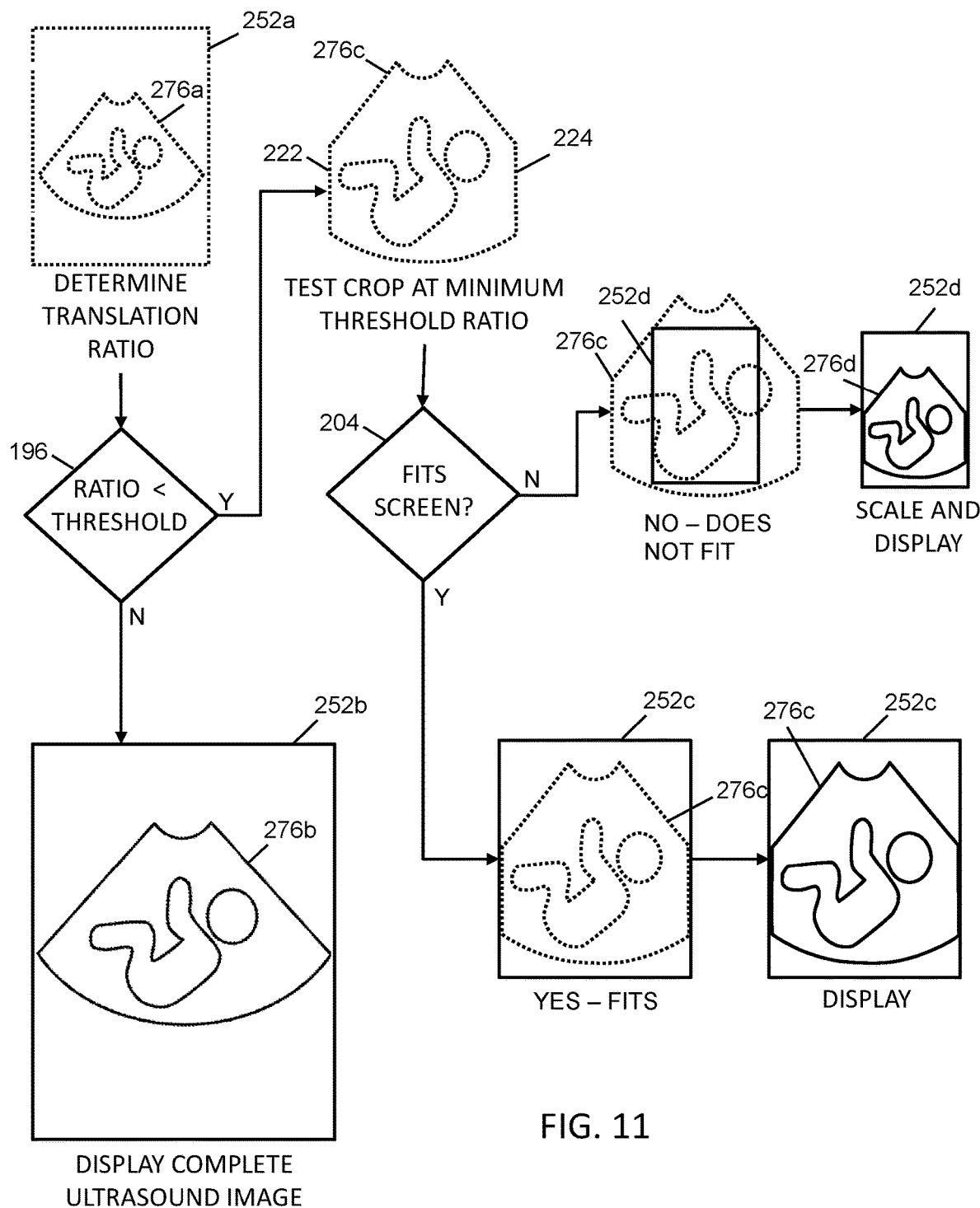
FIG. 11 is a schematic diagram illustrating the various steps in the third process when displaying a curvilinear ultrasound image on a screen in the portrait orientation, according to an embodiment of the present invention.
Figure 12:
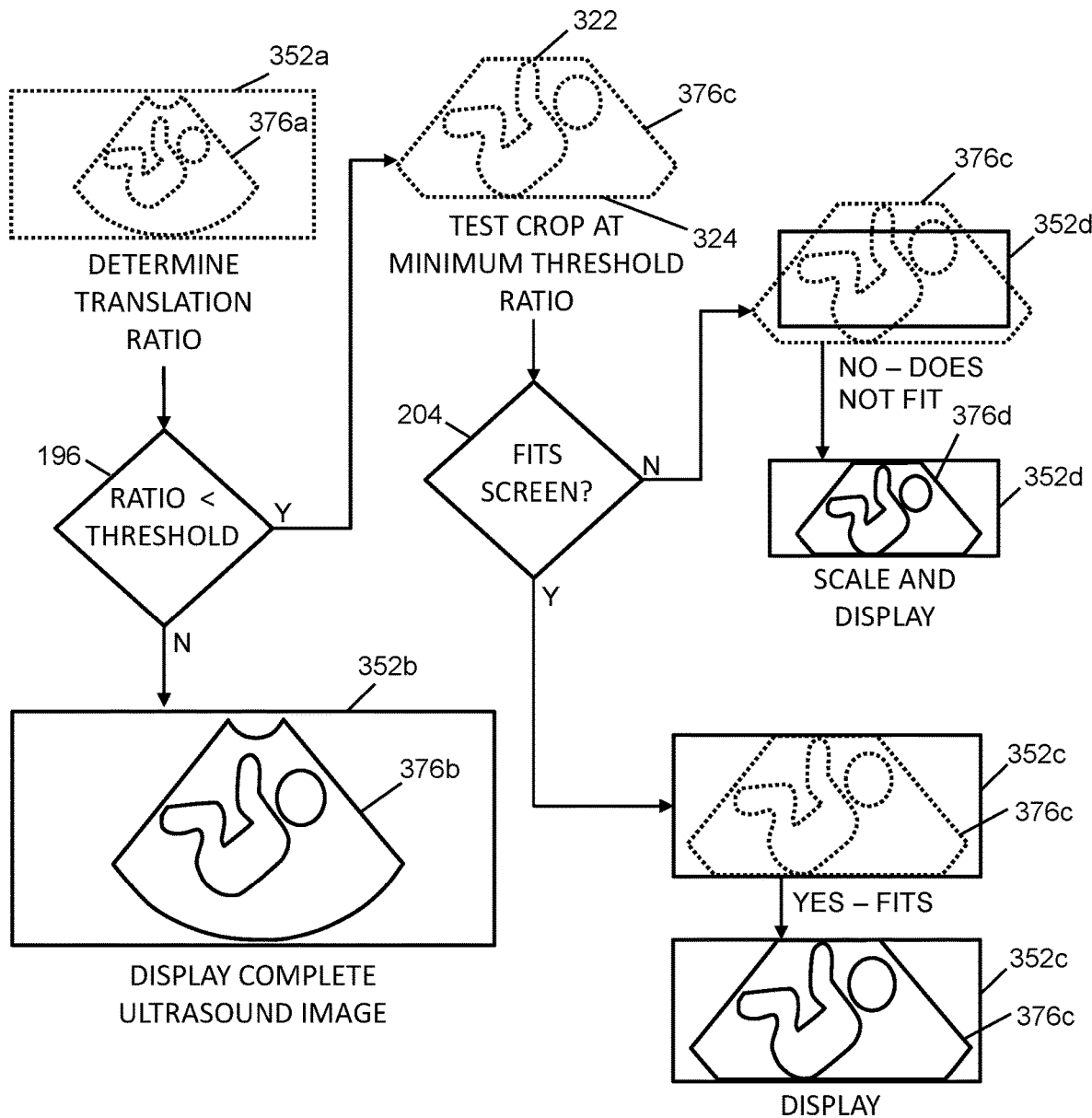
FIG. 12 is a schematic diagram illustrating the various steps in the third process when displaying to a curvilinear ultrasound image on a screen in the landscape orientation, according to an embodiment of the present invention.

FIGS. 10-12 below provide a number of example scenarios for how the method of FIG. 9 may be performed on different types of ultrasound images, and different types of screen sizes/orientations. In discussing FIGS. 10-12 below, reference will simultaneously be made to the method of FIG. 9.

Referring simultaneously to FIGS. 9 and 10, shown there is a pictorial illustration of the method of FIG. 9 for an example embodiment where a relatively superficial image is acquired using a linear scanner that produces a generally rectangular ultrasound image, and this image is displayed on a screen in portrait orientation. The translation ratio is first determined by determining the size of the ultrasound image 176a as if it were displayed in full on a given available screen area 152a (acts 190-194 of FIG. 9). As noted above, the translation ratio may be a physical distance on the screen occupied by a portion of the complete version of the ultrasound image (were it to be fitted to the available screen area 152a) divided by the corresponding physical distance of the scanned tissue.

In step 196, the translation ratio may be compared to a minimum translation ratio. If the determined translation ratio is not less than the minimum translation ratio (the 'N' branch at act 196—e.g., the available screen area is sufficiently large to display the imaged tissue in sufficient detail), the complete ultrasound image 176b may be displayed in full on the available screen area 152b.

While the example of FIG. 10 shows the ultrasound image 176b extended to occupy the full available width of the available screen area 152b, in some embodiments where the available display area 152b is particularly large, the complete ultrasound image 176b may be displayed without extending the image to the full width and/or height of the available screen area. In these embodiments, a maximum threshold translation ratio may be provided, so that if the complete ultrasound image 176b is to be displayed, it should have a translation ratio no larger than the maximum translation ratio. For example, this may result in blank space being provided adjacent to (e.g., to the left and/or right of) the ultrasound image 176b.

In situations where the available display area 152b is particularly large, extending the complete ultrasound image 176b to fill the available space may overly stretch the appearance of the ultrasound image 176b so that it appears pixelated. Having a maximum threshold translation ratio at which an ultrasound image 176b may be displayed may prevent this from occurring. In various example embodiments, for example, the maximum threshold translation ratio may be set to between 1-3.

Referring still to FIG. 10, if the translation ratio is below the minimum translation ratio (the 'Y' branch at act 196), a cropping operation may be performed on an ultrasound image which is translated to have the minimum threshold ratio (acts 200-202 of FIG. 9). As noted above, in some embodiments, during the cropping operation, such ultrasound image may be cropped at successively smaller crop ratios until a crop ratio limit is met. The cropping operation may generate cropped test ultrasound image 176c. In the illustrated example of FIG. 10, the sides 122, 124 of image 176c may be removed during the cropping operation.

Generally, for ultrasound images displayed on screens that are in portrait orientation, the limiting dimension of the screen is the width of the screen area. As a result, cropping may generally be done on one or more sides of the image to allow for the appearance of the ultrasound image to be magnified along the width dimension.

In step 204, it is determined whether the cropped test ultrasound image 176c fits the available area of a given screen. If it does (the 'Y' branch at act 204), e.g., if it fits in available screen area 152c, then the cropped test ultrasound image 176c may be displayed in the screen area 152c without scaling.

If the cropped test ultrasound image 176c does not fit (the 'N' branch at act 204), e.g., if it does not fit in available screen area 152d, then the cropped test ultrasound image is scaled and displayed as ultrasound image 176d. The 'N' branch of act 204 may usually be executed for smaller available screen areas 176d compared to other available screen areas.

When displaying images acquired using a linear image, it is atypical to perform any cropping. However, as discussed with respect to FIG. 10, the present embodiments may perform certain cropping (e.g., on the left and right sides of an ultrasound image) to try to maintain a higher translation ratio and show the details in the center portion of the image at greater magnification. This may be desirable, for example, when the linear image is generated in the context of an interventional procedure where the ultrasound image is being used to highlight a needle being inserted into tissue. For example, as compared to an image acquired without the present embodiments, the present embodiments may provide an image with a higher translation ratio that makes it easier for an ultrasound operator to more easily visualize the inserted needle. At the same time, the present embodiments do not simply keep cropping for successively smaller screens, in a manner that would crop out important aspects of the ultrasound image 176b. By cropping only up to a crop ratio limit and then scaling the cropped image from there to generate an image that can be displayed, the present embodiments provide an optimal balance between the desirability of having as high a translation ratio for the displayed image on the one hand (to make it as easy as possible to see detail in the ultrasound image) with the risk that over-cropping might actually remove parts of the image that is desired to be viewed by the operator.

Referring to FIG. 11, shown there is a pictorial illustration of the method of FIG. 9 for an example embodiment where a curvilinear image is displayed on a screen in portrait orientation. The translation ratio is first determined by determining the size of the ultrasound image 276a as if it were displayed in full on a given available screen area 252a (acts 190-194 of FIG. 9). As noted above, the translation ratio may be a physical distance on the screen occupied by a portion of the complete version of the ultrasound image (were it to be fitted to the available screen area 252a) divided by the corresponding physical distance of the scanned tissue.

In step 196, the translation ratio may be compared to a minimum translation ratio. If the determined translation ratio is not less than the minimum translation ratio (the 'N' branch at act 196—e.g., the available screen area is sufficiently large to display the imaged tissue in sufficient detail), the ultrasound image 276b may be displayed in full on the available screen area 252b. As with the illustration in FIG. 10, the ultrasound image 276a has a width that matches the width of the available screen area 252b. However, in some embodiments where the available screen area 252b is particularly large, the width of the ultrasound image 276b may be configured to be of a size that, when displayed, has a translation ratio no larger than a maximum translation ratio.

Referring still to FIG. 11, if the translation ratio is below the minimum translation ratio (the 'Y' branch at act 196), a cropped test ultrasound image 276c having the minimum threshold translation ratio may be generated from the cropping operation (acts 200-202 of FIG. 9). In the illustrated example of FIG. 11, the sides 222, 224 of image 276c may be removed during the cropping operation. As noted above with respect to FIG. 10, the cropped test ultrasound image 276c may be generated from a cropping operation that repeatedly crops the ultrasound image at successively smaller crop ratios up to a crop ratio limit.

In various embodiments, the crop ratio limit may differ for different types of ultrasound images (e.g., linear, sector, or curvilinear images as may be generated from transducers having different transducer geometries). For example, when cropping the left and right sides of an image, the portion of the ultrasound scan data that is removed may be higher for a linear image (where the entire length of the scan line data in the axial direction for the edge transducer elements are removed) than for a sector image or a curvilinear image (where only the deeper image data is removed while the shallower image data closer to the scan head is preserved). This can be seen comparing the portions of the curvilinear ultrasound image 222, 224 that are removed in FIG. 11 versus the portions of the linear ultrasound image 122, 124 which are removed in FIG. 10. Thus, since cropping may remove a higher proportionate amount of image data for a linear image than for a sector or curvilinear image, the crop ratio limit may be more constrained for linear images. Put another way, a linear image may not be as tolerable to cropping as curvilinear and sector images are. As such, in some embodiments, the crop ratio limit may be smaller for sector and/or curvilinear images (e.g., it may tolerate more cropping) since cropping may not remove as much relevant image data. For example, in various embodiments, a crop ratio limit may be between 85-95% for a linear image, and 75-85% for a sector and/or curvilinear image.

The discussion above with respect to cropping generally relates to cropping an image after scan conversion has been performed so as to fit image data that is in cartesian coordinates into a rectangular display. However, in various embodiments, cropping may additionally or alternatively be performed on pre-scan converted image data (e.g., to remove scan lines generated from the edges of the transducer). For example, for sector and curvilinear images, this data may still be in polar coordinate form when cropping is performed to remove the edgemost scanlines altogether.

Referring still to FIG. 11, at act 204, it is determined whether the cropped test ultrasound image 276c fits the available area of the screen. If it does (the 'Y' branch at act 204), e.g., if it fits in available screen area 252c, then the cropped test ultrasound image 276c may be displayed in the screen area 252c without scaling. If the cropped test ultrasound image 276c does not fit (the 'N' branch at act 204), e.g., if it does not fit in available screen area in available screen area 252d, then it is scaled and displayed as ultrasound image 276d. As was the case above in relation to the example of FIG. 10, the 'N' branch of act 204 may usually be executed for smaller available screen areas 252d compared to other available screen areas.

FIG. 11 illustrates how the method of FIG. 9 may be provide desirable results for a curvilinear image. A similar discussion may be applicable for sector a sector image. As with the example of FIG. 10, in FIG. 11, the present embodiments may perform certain cropping (e.g., on the left and right sides of an ultrasound image) to try to maintain a higher translation ratio and show the details in the center portion of the image at greater magnification. Since it is typical for the operator to center the transducer over the tissue desired to be viewed (e.g., whether the imaged tissue is of a fetus, cardiac function, or other internal organ), the cropping may allow the imaged tissue in the middle portion of the image to be more easily discerned.

At the same time, the present embodiments do not simply keep cropping for successively smaller screens, in a manner that would crop out important aspects of the ultrasound image 276b. By cropping only up to a crop ratio limit and then scaling the cropped image from there to generate an image that can be displayed, the present embodiments provide an optimal balance between the desirability of having as high a translation ratio for the displayed image on the one hand (to make it as easy as possible to see detail in the ultrasound image) with the risk that over-cropping might actually remove parts of the image that is desired to be viewed by the operator.

Referring now simultaneously to FIGS. 9 and 12, shown there is a pictorial illustration of the method of FIG. 9 for an example embodiment where a curvilinear image is displayed on a screen in landscape orientation. The translation ratio is first determined by determining the size of the ultrasound image 376a as if it were displayed in full on a given available screen area 352a (acts 190-194 of FIG. 9). As noted above, the translation ratio may be a physical distance on the screen occupied by a portion of the complete version of the ultrasound image (were it to be fitted to the available screen area 352a) divided by the corresponding physical distance of the scanned tissue.

In step 196, the translation ratio may be compared to a minimum translation ratio. If the determined translation ratio is not less than the minimum translation ratio (the 'N' branch at act 196—e.g., the available screen area is sufficiently large to display the imaged tissue in sufficient detail), the ultrasound image 376b may be displayed in full on the available screen area 352b.

Unlike the examples in FIGS. 10 and 11 above which displayed ultrasound images on a screen in portrait orientation, since the screen is in landscape orientation in FIG. 12, the limiting dimension of the screen is the height of available screen area as opposed to the width. As such, when displaying the complete ultrasound image 376b, the height of the ultrasound image 376b may be configured to match the available height of the available screen area 352b. To have the ultrasound image 376b maintain the same aspect ratio as ultrasound image 376a, there may be blank space provided to the left and right of the ultrasound image 376b.

As with the examples discussed above in relation to FIGS. 10 and 11, for particularly large screens, the height of the ultrasound image 376b may be configured to be of a size that, when displayed, has a translation ratio no larger than a maximum translation ratio. In these cases, there may also be blank space above and/or below the complete ultrasound image 376b.

Referring still to FIG. 12, if the translation ratio is below the minimum translation ratio (the 'Y' branch at act 196), a cropped test ultrasound image 376c having the minimum threshold translation ratio may be generated from the cropping operation (acts 200-202 of FIG. 9). In the illustrated example of FIG. 12, the top and bottom edges 322, 324 of image 376c may be removed. As noted above with respect to FIG. 10, the cropped test ultrasound image 376c may be generated from a cropping operation that repeatedly crops the ultrasound image at successively smaller crop ratios up to a crop ratio limit.

In the examples of FIGS. 10 and 11, cropping was generally performed on the sides of the ultrasound image when the ultrasound image is being displayed on a screen in portrait orientation. However, in the example embodiment of FIG. 12, the ultrasound image is being displayed in landscape orientation so that the limiting dimension of the screen is the height of the screen. In this scenario, it may be desirable to crop the top and/or bottom of the ultrasound image so that the vertical dimension of the ultrasound image can be shown in greater magnification.

At act 204, it is determined whether the cropped test ultrasound image 376c fits the available area of the screen. If it does (the 'Y' branch at act 204), e.g., if it fits in available screen area 352c, then the cropped test ultrasound image 376c may be displayed in the screen area 352c without scaling. If the cropped test ultrasound image 376c does not fit (the 'N' branch at act 204), e.g., if it does not fit in available screen area in available screen area 252d, then it is scaled and displayed as ultrasound image 376d. As was the case above in relation to the examples of FIGS. 10 and 11, the 'N' branch of act 204 may usually be executed for smaller available screen areas 352d compared to other available screen areas.

FIG. 12 illustrates how the method of FIG. 9 may again provide desirable results for a curvilinear image when it is displayed in portrait orientation. A similar discussion may be applicable for sector a sector image. As with the examples of FIGS. 10 and 11 above, the present embodiments may perform certain cropping to try to maintain a higher translation ratio and show the details in the center portion of the image at greater magnification. However, since the screen is positioned in a landscape orientation, the limiting dimension of the screen is the height of the screen. As such, it is certain top and/or bottom portions 322, 324 of the ultrasound image 376c that may be removed. This may allow the vertically-center portion of the ultrasound image 376c to be shown in a way where imaged tissue therein may be more easily discernible.

Again, having a crop ratio limit may reduce the possibility that there is excessive cropping that would crop out important aspects of the ultrasound image 376b. By cropping only up to a crop ratio limit and then scaling the cropped image from there to generate an image that can be displayed, the present embodiments are applicable also to display of an ultrasound image in landscape orientation, so as to provide an optimal balance between the desirability of having as high a translation ratio for the displayed image on the one hand (to make it as easy as possible to see detail in the ultrasound image) with the risk that over-cropping might actually remove parts of the image that is desired to be viewed by the operator.

While the foregoing description has been given largely in terms of ultrasound images, it is also applicable to ultrasound media in general.

In some embodiments, the same ultrasound scanning parameters may be used for all application window sizes or, as discussed above, different sets of scan parameters may be used depending on the application window and/or screen size.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, support assembly, valve device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and subcombinations as may reasonably be inferred. The scope of the claims should not be limited by the embodiments set forth in the examples but should be given the broadest interpretation consistent with the description as a whole.

C. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The term "corresponds" in relation to the display of an ultrasound image in an application window means that a particular dimension of the displayed ultrasound image is equal, to within a tolerance of 10% or an equivalent number of pixels, to a specified dimension of the application window.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

D. Claim Support

Disclosed herein is a method for displaying an ultrasound image comprising: determining, by a processor, a vertical dimension of an application window displayed on a screen to which an ultrasound scanner is connected, when the application window is in portrait mode; comparing, by the processor, the vertical dimension to a first threshold dimension; when the vertical dimension is greater than the first threshold dimension, displaying a complete ultrasound image in the application window, the complete ultrasound image scaled so that a full width of the displayed complete ultrasound image corresponds to a width of the application window; and when the vertical dimension is less than the first threshold dimension, displaying a cropped ultrasound image in the application window scaled so that a full height of the cropped ultrasound image is displayed and at least one side edge of the complete ultrasound image is not displayed.

In some embodiments, the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

In some embodiments, the method includes, prior to the comparing, by the processor, the vertical dimension to the first threshold dimension, determining whether the imaging depth of the ultrasound image is greater than a threshold imaging depth; wherein when the imaging depth of the ultrasound image is greater than the threshold imaging depth, performing the comparing and subsequent steps; and when the imaging depth of the ultrasound image is determined to be less than the threshold imaging depth, scaling the complete ultrasound image so that the full width of the complete ultrasound image corresponds to the width of the application window, and displaying the scaled complete ultrasound image.

In some embodiments, the method includes, when the vertical dimension is less than the first threshold dimension: comparing, by the processor, the vertical dimension to a second threshold dimension different from the first threshold dimension; when the vertical dimension is less than the second threshold dimension, displaying the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scaling the displayed ultrasound image so that the full height of the displayed ultrasound image corresponds to the second threshold dimension.

In some embodiments, the complete ultrasound image displayed in the application window corresponds to the width of the application window only if the width of the application window is below a threshold width; and when the width of the application window is above the threshold width, the complete ultrasound image is scaled and displayed so that the width of the displayed ultrasound image corresponds to the threshold width.

In some embodiments, the method includes instructing, by the processor, the ultrasound scanner to acquire ultrasound scan data, wherein: the ultrasound scan data is acquired using a first set of parameters when the vertical dimension of the application window displayed on the screen is greater than the first threshold dimension; and the ultrasound scan data is acquired using a second set of parameters when the vertical dimension of the application window displayed on the screen is less than the first threshold dimension.

In some embodiments, the first set of parameters comprises a first number of ultrasound signal scan lines and the second set of parameters comprises a second number of ultrasound signal scan lines, and the first number of ultrasound scan lines is different from the second number of ultrasound signal scan lines.

In some embodiments, the first set of parameters comprises a first frame rate and the second set of parameters comprises a second frame rate, and the first frame rate is different from the second frame rate.

In some embodiments, the method includes instructing, by the processor, the ultrasound scanner to acquire ultrasound scan data, wherein: the ultrasound scan data is processed through an enhanced smoothing filter when the vertical dimension of the application window displayed on the screen is greater than the first threshold dimension; and the ultrasound scan data is processed through a regular smoothing filter when the vertical dimension of the application window displayed on the screen is less than the first threshold dimension.

In some embodiments, the method includes instructing, by the processor, the ultrasound scanner to acquire ultrasound scan data, wherein: the ultrasound scan data is processed through an enhanced speckle reduction process when the vertical dimension of the application window displayed on the screen is greater than the first threshold dimension; and the ultrasound scan data is processed through a regular speckle reduction process when the vertical dimension of the application window displayed on the screen is less than the first threshold dimension.

In some embodiments, the method includes, when the vertical dimension is greater than the threshold dimension and where the display of the complete ultrasound image scaled so that a full width of the displayed complete ultrasound image corresponds to a width of the application window results in unoccupied space in the application window, displaying additional information or user interface controls in the unoccupied space of the application window.

In some embodiments, the method includes displaying in the application window: a first graphical user interface when the vertical dimension of the application window displayed on the screen is greater than the first threshold dimension; and a second graphical user interface when the vertical dimension of the application window displayed on the screen is less than the first threshold dimension.

In some embodiments, the method includes determining that the application window is in landscape mode and, in response thereto, scaling the ultrasound image so that the complete ultrasound image is displayed.

Also disclosed herein is a computer readable medium comprising computer readable instructions, which, when executed by a processor cause a display device to: determine a vertical dimension of an application window displayed on a screen to which an ultrasound scanner is connected, when the application window is in portrait mode; compare the vertical dimension to a first threshold dimension; when the vertical dimension is greater than the threshold dimension, display a complete ultrasound image on the application window, the complete ultrasound image scaled so that a full width of the displayed complete ultrasound image corresponds to a width of the application window; and when the vertical dimension is less than the first threshold dimension, display a cropped ultrasound image in the application window scaled so that a full height of the cropped ultrasound image is displayed and at least one side edge of the complete ultrasound image is not displayed.

In some embodiments, the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

In some embodiments, the computer readable instructions, when executed by the processor, cause the display device to: prior to the comparing of the vertical dimension to the first threshold dimension, determine whether the imaging depth of the ultrasound image is greater than a threshold imaging depth; wherein when the imaging depth of the ultrasound image is greater than the threshold imaging depth, perform the comparing and subsequent steps; and when the imaging depth of the ultrasound image is determined to be less than the threshold imaging depth, scale the complete ultrasound image so that the full width of the complete ultrasound image corresponds to the width of the application window, and display the scaled complete ultrasound image.

In some embodiments, the computer readable instructions, when executed by the processor, cause, when the vertical dimension is less than the first threshold dimension, the display device to: compare the vertical dimension to a second threshold dimension different from the first threshold dimension; when the vertical dimension is less than the second threshold dimension, display the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scale the displayed ultrasound image so that the full height of the displayed ultrasound image corresponds to the second threshold dimension.

In some embodiments, the complete ultrasound image displayed in the application window corresponds to the width of the application window only if the width of the application window is below a threshold width; and when the width of the application window is above the threshold width, the complete ultrasound image is scaled and displayed so that the width of the displayed ultrasound image corresponds to the threshold width.

In some embodiments, the computer readable instructions, when executed by the processor, cause the ultrasound scanner to acquire ultrasound scan data, wherein: the ultrasound scan data is acquired using a first set of parameters when the vertical dimension of the application window displayed on the screen is greater than the first threshold dimension; and the ultrasound scan data is acquired using a second set of parameters when the vertical dimension of the application window displayed on the screen is less than the first threshold dimension.

In some embodiments, the first set of parameters comprises a first number of ultrasound signal scan lines and the second set of parameters comprises a second number of ultrasound signal scan lines, and the first number of ultrasound scan lines is different from the second number of ultrasound signal scan lines.

In some embodiments, the first set of parameters comprises a first frame rate and the second set of parameters comprises a second frame rate, and the first frame rate is different from the second frame rate.

In some embodiments, the computer readable instructions, when executed by the processor, cause the ultrasound scanner to acquire ultrasound scan data, wherein: the ultrasound scan data is processed through an enhanced smoothing filter when the vertical dimension of the application window displayed on the screen is greater than the first threshold dimension; and the ultrasound scan data is processed through a regular smoothing filter when the vertical dimension of the application window displayed on the screen is less than the first threshold dimension.

In some embodiments, the computer readable instructions, when executed by the processor, cause the ultrasound scanner to acquire ultrasound scan data, wherein: the ultrasound scan data is processed through an enhanced speckle reduction process when the vertical dimension of the application window displayed on the screen is greater than the first threshold dimension; and the ultrasound scan data is processed through a regular speckle reduction process when the vertical dimension of the application window displayed on the screen is less than the first threshold dimension.

In some embodiments, the computer readable instructions, when executed by the processor, cause, when the vertical dimension is greater than the threshold dimension and where the display of the complete ultrasound image scaled so that a full width of the displayed complete ultrasound image corresponds to a width of the application window results in unoccupied space in the application window, the display device to display additional information or user interface controls in the unoccupied space of the application window.

In some embodiments, the computer readable instructions, when executed by the processor, cause the display device to display in the application window: a first graphical user interface when the vertical dimension of the application window displayed on the screen is greater than the first threshold dimension; and a second graphical user interface when the vertical dimension of the application window displayed on the screen is less than the first threshold dimension.

In some embodiments, the computer readable instructions, when executed by the processor, cause the display device to determine that the application window is in landscape mode and, in response thereto, scale the ultrasound image so that the complete ultrasound image is displayed.

Further disclosed herein is an ultrasound scanning system comprising: an ultrasound scanner; a display device connected to the ultrasound scanner; and a computer readable medium in the display device comprising computer readable instructions, which, when executed by a processor cause the display device to: determine a vertical dimension of an application window displayed on a screen to which an ultrasound scanner is connected, when the application window is in portrait mode; compare the vertical dimension to a first threshold dimension; when the vertical dimension is greater than the threshold dimension, display a complete ultrasound image on the application window, the complete ultrasound image scaled so that a full width of the displayed complete ultrasound image corresponds to a width of the application window; and when the vertical dimension is less than the first threshold dimension, display a cropped ultrasound image in the application window scaled so that a full height of the cropped ultrasound image is displayed and at least one side edge of the complete ultrasound image is not displayed.

In some embodiments, the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

In some embodiments, the computer readable instructions, when executed by the processor, cause the display device to: prior to the comparing of the vertical dimension to the first threshold dimension, determine whether the imaging depth of the ultrasound image is greater than a threshold imaging depth; wherein when the imaging depth of the ultrasound image is greater than the threshold imaging depth, perform the comparing and subsequent steps; and when the imaging depth of the ultrasound image is determined to be less than the threshold imaging depth, scale the complete ultrasound image so that the full width of the complete ultrasound image corresponds to the width of the application window, and display the scaled complete ultrasound image.

In some embodiments, the computer readable instructions, when executed by the processor, cause, when the vertical dimension is less than the first threshold dimension, the display device to: compare the vertical dimension to a second threshold dimension different from the first threshold dimension; when the vertical dimension is less than the second threshold dimension, display the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scale the displayed ultrasound image so that the full height of the displayed ultrasound image corresponds to the second threshold dimension.

In some embodiments, the complete ultrasound image displayed in the application window corresponds to the width of the application window only if the width of the application window is below a threshold width; and when the width of the application window is above the threshold width, the complete ultrasound image is scaled and displayed so that the width of the displayed ultrasound image corresponds to the threshold width.

In some embodiments, the computer readable instructions, when executed by the processor, cause the ultrasound scanner to acquire ultrasound scan data, wherein: the ultrasound scan data is acquired using a first set of parameters when the vertical dimension of the application window displayed on the screen is greater than the first threshold dimension; and the ultrasound scan data is acquired using a second set of parameters when the vertical dimension of the application window displayed on the screen is less than the first threshold dimension.

In some embodiments, the first set of parameters comprises a first number of ultrasound signal scan lines and the second set of parameters comprises a second number of ultrasound signal scan lines, and the first number of ultrasound scan lines is different from the second number of ultrasound signal scan lines.

In some embodiments, the first set of parameters comprises a first frame rate and the second set of parameters comprises a second frame rate, and the first frame rate is different from the second frame rate.

In some embodiments, the computer readable instructions, when executed by the processor, cause the ultrasound scanner to acquire ultrasound scan data, wherein: the ultrasound scan data is processed through an enhanced smoothing filter when the vertical dimension of the application window displayed on the screen is greater than the first threshold dimension; and the ultrasound scan data is processed through a regular smoothing filter when the vertical dimension of the application window displayed on the screen is less than the first threshold dimension.

In some embodiments, the computer readable instructions, when executed by the processor, cause the ultrasound scanner to acquire ultrasound scan data, wherein: the ultrasound scan data is processed through an enhanced speckle reduction process when the vertical dimension of the application window displayed on the screen is greater than the first threshold dimension; and the ultrasound scan data is processed through a regular speckle reduction process when the vertical dimension of the application window displayed on the screen is less than the first threshold dimension.

In some embodiments, the computer readable instructions, when executed by the processor, cause, when the vertical dimension is greater than the threshold dimension and where the display of the complete ultrasound image scaled so that a full width of the displayed complete ultrasound image corresponds to a width of the application window results in unoccupied space in the application window, the display device to display additional information or user interface controls in the unoccupied space of the application window.

In some embodiments, the computer readable instructions, when executed by the processor, cause the display device to display in the application window: a first graphical user interface when the vertical dimension of the application window displayed on the screen is greater than the first threshold dimension; and a second graphical user interface when the vertical dimension of the application window displayed on the screen is less than the first threshold dimension.

In some embodiments, the computer readable instructions, when executed by the processor, cause the display device to determine that the application window is in landscape mode and, in response thereto, scale the ultrasound image so that the complete ultrasound image is displayed.

Also disclosed is a method for adapting display of an ultrasound image on a display device, the ultrasound image being generated from ultrasound signals transmitted and received by an ultrasound scanner, the method comprising: determining a physical distance traversed by the ultrasound signals to generate the ultrasound image; determining a translation ratio for translating the physical distance traversed by the ultrasound signals to a corresponding physical distance on a screen of the display device, were the ultrasound image be fitted to an available physical area of the screen of the display device; if the determined translation ratio is less than a minimum threshold translation ratio, generating a test ultrasound image at the minimum threshold translation ratio, performing a cropping operation on the test ultrasound image to generate a cropped test ultrasound image, and determining if the cropped test ultrasound image fits the available physical area of the screen of the display device; if the cropped test ultrasound image does not fit the available physical area of the screen of the display device, scaling the cropped test ultrasound image generated from the cropping operation so that the scaled and cropped test ultrasound image is fitted to the available physical area of the screen of the display device; and displaying the scaled and cropped test ultrasound image within the available physical area of the screen of the display device.

In some embodiments, if the cropped test ultrasound image fits the available physical area of the screen of the display device for displaying the ultrasound image, displaying the cropped test ultrasound image in the available physical area of the screen of the display device.

In some embodiments, the cropping operation comprises: cropping the test ultrasound image at a first crop ratio; if the test ultrasound image cropped at the first crop ratio fits the available physical area of the screen of the display device for displaying the ultrasound image, displaying the test ultrasound image cropped at the first crop ratio in the available physical area of the screen of the display device; if the test ultrasound image cropped at the first crop ratio does not fit the available physical area of the screen of the display device, then, prior to the scaling: further cropping the test ultrasound image cropped at the first crop ratio, to generate the test ultrasound image cropped at a second crop ratio; if the test ultrasound image cropped at the second crop ratio fits the available physical area of the screen of the display device for displaying the ultrasound image, displaying the test ultrasound image cropped at the second crop ratio in the available physical area of the screen of the display device; if the test ultrasound image cropped at the second crop ratio does not fit the available physical area of the screen of the display device for displaying the ultrasound image, providing the test ultrasound image cropped at the second crop ratio as the cropped test ultrasound image for the displaying step subsequent to the scaling step.

In some embodiments, the method according to claim 1, wherein the cropping operation comprises: repeatedly: cropping the test ultrasound image at a test crop ratio, determining whether the test ultrasound image cropped at the test crop ratio fits the available physical area of the screen of the display device for displaying the ultrasound image, and if the test ultrasound image cropped at the test crop ratio fits the available physical area of the screen of the display device for displaying the ultrasound image, displaying the test ultrasound image cropped at the test crop ratio in the available physical area of the screen of the display device, for successively smaller test crop ratios, until a crop ratio limit is met; if the test ultrasound image cropped at the crop ratio limit does not fit the available physical area of the screen of the display device, providing the test ultrasound image cropped at the crop ratio limit as the cropped test ultrasound image generated from the cropping operation.

In some embodiments, the cropping operation comprises cropping the test ultrasound image on at least one side edge of the test ultrasound image.

In some embodiments, the cropping operation comprises cropping the test ultrasound image on a top edge of the test ultrasound image.

In some embodiments, when scaling the cropped test ultrasound image, the method further comprises scaling the cropped test ultrasound image generated from the cropping operation so that a vertical dimension of the scaled and cropped test ultrasound image substantially matches a vertical dimension of the available physical area of the screen of the display device.

In some embodiments, when scaling the cropped test ultrasound image, an aspect ratio of the scaled and cropped test ultrasound image matches an aspect ratio of the ultrasound image.

In some embodiments, if the determined translation ratio is greater than the minimum threshold translation ratio, the method further comprises: determining whether the determined translation ratio exceeds a maximum threshold translation ratio; if the determined translation ratio exceeds the maximum threshold translation ratio, scaling the ultrasound image so that the scaled ultrasound image has the maximum threshold translation ratio; and displaying the scaled ultrasound image having the maximum threshold translation ratio in the available physical area of the screen of the display device.

Also disclosed is a computer readable medium comprising computer readable instructions which, when executed by a processor of a display device that is communicably coupled to an ultrasound scanner, configure the display device to: determine a physical distance traversed by ultrasound signals that are transmitted and received by the ultrasound scanner to generate an ultrasound image; determine a translation ratio for translating the physical distance traversed by the ultrasound signals to a corresponding physical distance on a screen of the display device, were the ultrasound image be fitted to an available physical area of the screen of the display device; if the determined translation ratio is less than a minimum threshold translation ratio, generate a test ultrasound image at the minimum threshold translation ratio, perform a cropping operation on the test ultrasound image to generate a cropped test ultrasound image, and determine if the cropped test ultrasound image fits the available physical area of the screen of the display device; if the cropped test ultrasound image does not fit the available physical area of the screen of the display device, scale the cropped test ultrasound image generated from the cropping operation so that the scaled and cropped test ultrasound image is fitted to the available physical area of the screen of the display device; and display the scaled and cropped test ultrasound image within the available physical area of the screen of the display device.

In some embodiments, if the cropped test ultrasound image fits the available physical area of the screen of the display device for displaying the ultrasound image, the processor configures the display device to display the cropped test ultrasound image in the available physical area of the screen of the display device.

In some embodiments, when performing the cropping operation, the processor further configures the display device to: crop the test ultrasound image at a first crop ratio; if the test ultrasound image cropped at the first crop ratio fits the available physical area of the screen of the display device for displaying the ultrasound image, display the test ultrasound image cropped at the first crop ratio in the available physical area of the screen of the display device; if the test ultrasound image cropped at the first crop ratio does not fit the available physical area of the screen of the display device, then, prior to the scaling: further crop the test ultrasound image cropped at the first crop ratio, to generate the test ultrasound image cropped at a second crop ratio; if the test ultrasound image cropped at the second crop ratio fits the available physical area of the screen of the display device for displaying the ultrasound image, display the test ultrasound image cropped at the second crop ratio in the available physical area of the screen of the display device; if the test ultrasound image cropped at the second crop ratio does not fit the available physical area of the screen of the display device for displaying the ultrasound image, provide the test ultrasound image cropped at the second crop ratio as the cropped test ultrasound image for the displaying step subsequent to the scaling step.

In some embodiments, when performing the cropping operation, the processor further configures the display device to: repeatedly: crop the test ultrasound image at a test crop ratio, determine whether the test ultrasound image cropped at the test crop ratio fits the available physical area of the screen of the display device for displaying the ultrasound image, and if the test ultrasound image cropped at the test crop ratio fits the available physical area of the screen of the display device for displaying the ultrasound image, display the test ultrasound image cropped at the test crop ratio in the available physical area of the screen of the display device, for successively smaller test crop ratios, until a crop ratio limit is met; if the test ultrasound image cropped at the crop ratio limit does not fit the available physical area of the screen of the display device, provide the test ultrasound image cropped at the crop ratio limit as the cropped test ultrasound image generated from the cropping operation.

In some embodiments, when performing the cropping operation, the processor further configures the display device to crop the test ultrasound image on at least one side edge of the test ultrasound image.

In some embodiments, when performing the cropping operation, the processor further configures the display device to crop the test ultrasound image on a top edge of the test ultrasound image.

In some embodiments, when scaling the cropped test ultrasound image, the processor configures the display device to scale the cropped test ultrasound image generated from the cropping operation so that a vertical dimension of the scaled and cropped test ultrasound image substantially matches a vertical dimension of the available physical area of the screen of the display device.

In some embodiments, when scaling the cropped test ultrasound image, an aspect ratio of the scaled and cropped test ultrasound image matches an aspect ratio of the ultrasound image.

In some embodiments, if the determined translation ratio is greater than the minimum threshold translation ratio, the processor further configures the display device to: determine whether the determined translation ratio exceeds a maximum threshold translation ratio; if the determined translation ratio exceeds the maximum threshold translation ratio, scale the ultrasound image so that the scaled ultrasound image has the maximum threshold translation ratio; and display the scaled ultrasound image having the maximum threshold translation ratio in the available physical area of the screen of the display device.

Also disclosed herein is an ultrasound scanning system comprising: an ultrasound scanner configured to transmit and receive ultrasound signals to generate an ultrasound image; a display device communicably coupled to the ultrasound scanner, the display device being configured to: determine a physical distance traversed by the ultrasound signals to generate the ultrasound image; determine a translation ratio for translating the physical distance traversed by the ultrasound signals to a corresponding physical distance on a screen of the display device, were the ultrasound image be fitted to an available physical area of the screen of the display device; if the determined translation ratio is less than a minimum threshold translation ratio, generate a test ultrasound image at the minimum threshold translation ratio, perform a cropping operation on the test ultrasound image to generate a cropped test ultrasound image, and determine if the cropped test ultrasound image fits the available physical area of the screen of the display device; if the cropped test ultrasound image does not fit the available physical area of the screen of the display device, scale the cropped test ultrasound image generated from the cropping operation so that the scaled and cropped test ultrasound image is fitted to the available physical area of the screen of the display device; and display the scaled and cropped test ultrasound image within the available physical area of the screen of the display device.

In some embodiments, if the cropped test ultrasound image fits the available physical area of the screen of the display device for displaying the ultrasound image, the display device is further configured to display the cropped test ultrasound image in the available physical area of the screen of the display device.

In some embodiments, when performing the cropping operation, the display device is further configured to: crop the test ultrasound image at a first crop ratio; if the test ultrasound image cropped at the first crop ratio fits the available physical area of the screen of the display device for displaying the ultrasound image, display the test ultrasound image cropped at the first crop ratio in the available physical area of the screen of the display device; if the test ultrasound image cropped at the first crop ratio does not fit the available physical area of the screen of the display device, then, prior to the scaling: further crop the test ultrasound image cropped at the first crop ratio, to generate the test ultrasound image cropped at a second crop ratio; if the test ultrasound image cropped at the second crop ratio fits the available physical area of the screen of the display device for displaying the ultrasound image, display the test ultrasound image cropped at the second crop ratio in the available physical area of the screen of the display device; if the test ultrasound image cropped at the second crop ratio does not fit the available physical area of the screen of the display device for displaying the ultrasound image, provide the test ultrasound image cropped at the second crop ratio as the cropped test ultrasound image for the displaying step subsequent to the scaling step.

In some embodiments, when performing the cropping operation, the display device is further configured to: repeatedly: crop the test ultrasound image at a test crop ratio, determine whether the test ultrasound image cropped at the test crop ratio fits the available physical area of the screen of the display device for displaying the ultrasound image, and if the test ultrasound image cropped at the test crop ratio fits the available physical area of the screen of the display device for displaying the ultrasound image, display the test ultrasound image cropped at the test crop ratio in the available physical area of the screen of the display device, for successively smaller test crop ratios, until a crop ratio limit is met; if the test ultrasound image cropped at the crop ratio limit does not fit the available physical area of the screen of the display device, provide the test ultrasound image cropped at the crop ratio limit as the cropped test ultrasound image generated from the cropping operation.

In some embodiments, when performing the cropping operation, the display device is further configured to crop the test ultrasound image on at least one side edge of the test ultrasound image.

In some embodiments, when performing the cropping operation, the display device is further configured to crop the test ultrasound image on a top edge of the test ultrasound image.

In some embodiments, when scaling the cropped test ultrasound image, the display device is further configured to scale the cropped test ultrasound image generated from the cropping operation so that a vertical dimension of the scaled and cropped test ultrasound image substantially matches a vertical dimension of the available physical area of the screen of the display device.

In some embodiments, when scaling the cropped test ultrasound image, an aspect ratio of the scaled and cropped test ultrasound image matches an aspect ratio of the ultrasound image.

In some embodiments, if the determined translation ratio is greater than the minimum threshold translation ratio, the display device is further configured to: determine whether the determined translation ratio exceeds a maximum threshold translation ratio; if the determined translation ratio exceeds the maximum threshold translation ratio, scale the ultrasound image so that the scaled ultrasound image has the maximum threshold translation ratio; and display the scaled ultrasound image having the maximum threshold translation ratio in the available physical area of the screen of the display device.

The invention claimed is:

1. A method for displaying an ultrasound image comprising:
  determining, by a processor, a vertical dimension of an application window displayed on a screen to which an ultrasound scanner is connected, when the application window is in portrait mode; comparing, by the processor, the vertical dimension to a first threshold dimension; when the vertical dimension is greater than the threshold dimension, displaying a complete ultrasound image on the application window, the complete ultrasound image scaled so that a full width of the displayed complete ultrasound image corresponds to a width of the application window; and when the vertical dimension is less than or equal to the first threshold dimension, displaying a cropped ultrasound image on the application window scaled so that a full height of the cropped ultrasound image is displayed and at least one side edge of the complete ultrasound image is not displayed.

2. The method according to claim 1, wherein the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

3. The method according to claim 1, wherein prior to the comparing, by the processor, the vertical dimension to the first threshold dimension, determining whether the imaging depth of the ultrasound image is greater than a threshold imaging depth; wherein when the imaging depth of the ultrasound image is greater than the threshold imaging depth, performing the comparing and subsequent steps; and when the imaging depth of the ultrasound image is determined to be less than or equal to the threshold imaging depth, scaling the complete ultrasound image so that the full width of the complete ultrasound image corresponds to the width of the application window, and displaying the scaled complete ultrasound image.

4. The method according to claim 1, comprising, when the vertical dimension is less than or equal to the first threshold dimension:
comparing, by the processor, the vertical dimension to a second threshold dimension different from the first threshold dimension; when the vertical dimension is less than or equal to the second threshold dimension, displaying the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scaling the displayed ultrasound image so that the full height of the displayed ultrasound image corresponds to the second threshold dimension.

5. The method according to claim 1, wherein:
the complete ultrasound image displayed on the application window corresponds to the width of the application window only if the width of the application window is below a threshold width; and when the width of the application window is above the threshold width, the complete ultrasound image is scaled and displayed so that the width of the displayed ultrasound image corresponds to the threshold width.

6. The method according to claim 1, further comprising instructing, by the processor, the ultrasound scanner to acquire ultrasound scan data, wherein:
the ultrasound scan data is acquired using a first set of parameters when the vertical dimension of the application window displayed on the screen is greater than the first threshold dimension; and
the ultrasound scan data is acquired using a second set of parameters when the vertical dimension of the application window displayed on the screen is less than or equal to the first threshold dimension.

7. The method of claim 6, wherein the first set of parameters comprises a first number of ultrasound signal scan lines and the second set of parameters comprises a second number of ultrasound signal scan lines, and the first number of ultrasound scan lines is different from the second number of ultrasound signal scan lines.

8. The method of claim 6, wherein the first set of parameters comprises a first frame rate and the second set of parameters comprises a second frame rate, and the first frame rate is different from the second frame rate.

9. The method according to claim 1, comprising instructing, by the processor, the ultrasound scanner to acquire ultrasound scan data, wherein:
the ultrasound scan data is processed through an enhanced smoothing filter when the vertical dimension of the application window displayed on the screen is greater than the first threshold dimension; and
the ultrasound scan data is processed through a regular smoothing filter when the vertical dimension of the application window displayed on the screen is less than or equal to the first threshold dimension.

10. The method according to claim 1, comprising instructing, by the processor, the ultrasound scanner to acquire ultrasound scan data, wherein:
the ultrasound scan data is processed through an enhanced speckle reduction process when the vertical dimension of the application window displayed on the screen is greater than the first threshold dimension; and
the ultrasound scan data is processed through a regular speckle reduction process when the vertical dimension of the application window displayed on the screen is less than or equal to the first threshold dimension.

11. The method according to claim 1 comprising, when the vertical dimension is greater than the threshold dimension and where the display of the complete ultrasound image scaled so that a full width of the displayed complete ultrasound image corresponds to a width of the application window results in unoccupied space in the application window, displaying additional information or user interface controls on the occupied space of the application window.

12. The method according to claim 1, comprising displaying on the screen:
a first graphical user interface when the vertical dimension of the application window displayed on the screen is greater than the first threshold dimension; and
a second graphical user interface when the vertical dimension of the application window displayed on the screen is less than or equal to the first threshold dimension.

13. The method according to claim 1, comprising determining that the screen is in landscape mode and, in response thereto, scaling the ultrasound image so that the complete ultrasound image is displayed.

14. A computer readable medium comprising computer readable instructions, which, when executed by a processor cause a display device to:
determine a vertical dimension of a screen to which an ultrasound scanner is connected, when the screen is in portrait mode;
compare the vertical dimension to a threshold dimension;
when the vertical dimension is greater than the threshold dimension, display a complete ultrasound image on the screen scaled so that a width of the displayed ultrasound image corresponds to a width of the screen; and
when the vertical dimension is less than the threshold dimension, crop left and right sides of the complete ultrasound image and scale and display the cropped ultrasound image so that a width of the displayed cropped ultrasound image corresponds to a width of the screen and a height of the cropped ultrasound image is displayed;

wherein the ultrasound image has a depth greater than a threshold depth.

15. The computer readable medium of claim 14 wherein the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

16. The computer readable medium of claim 14 wherein prior to the comparing, by the processor, the vertical dimension to the first threshold dimension, determining whether the imaging depth of the ultrasound image is greater than a threshold imaging depth; wherein when the imaging depth of the ultrasound image is greater than the threshold imaging depth, performing the comparing and subsequent steps; and when the imaging depth of the ultrasound image is determined to be less than or equal to the threshold imaging depth, scaling the complete ultrasound image so that the full width of the complete ultrasound image corresponds to the width of the application window, and displaying the scaled complete ultrasound image.

17. The computer readable medium of claim 14 wherein the vertical dimension is less than or equal to the first threshold dimension: comparing, by the processor, the vertical dimension to a second threshold dimension different from the first threshold dimension; when the vertical dimension is less than or equal to the second threshold dimension, displaying the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scaling the displayed ultrasound image so that the full height of the displayed ultrasound image corresponds to the second threshold dimension.

18. An ultrasound scanning system comprising:
an ultrasound scanner;
a display device connected to the ultrasound scanner; and
a computer readable medium in the display device comprising computer readable instructions, which, when executed by a processor cause the display device to:
determine a vertical dimension of a screen to which an ultrasound scanner is connected, when the screen is in portrait mode;
compare the vertical dimension to a threshold dimension;
when the vertical dimension is greater than the threshold dimension, display a complete ultrasound image on the screen scaled so that a width of the displayed ultrasound image corresponds to a width of the screen; and
when the vertical dimension is less than the threshold dimension, crop left and right sides of the complete ultrasound image and scale and display the cropped ultrasound image so that a width of the displayed cropped ultrasound image corresponds to a width of the screen and a height of the cropped ultrasound image is displayed;
wherein the ultrasound image has a depth greater than a threshold depth.

19. The ultrasound scanning system of claim 18 wherein the complete ultrasound image is generated from a plurality of radial ultrasound signal lines, and each of the plurality of radial ultrasound signal lines comprises image data at an imaging depth, and wherein the full width of the displayed complete ultrasound image comprises image data at the imaging depth for the leftmost and rightmost radial ultrasound signal lines of the plurality of radial ultrasound signal lines.

20. The ultrasound scanning system of claim 18 wherein prior to the processor comparing the vertical dimension to the first threshold dimension, determining whether the imaging depth of the ultrasound image is greater than a threshold imaging depth; wherein when the imaging depth of the ultrasound image is greater than the threshold imaging depth, performing the comparing and subsequent steps; and when the imaging depth of the ultrasound image is determined to be less than or equal to the threshold imaging depth, scaling the complete ultrasound image so that the full width of the complete ultrasound image corresponds to the width of the application window, and displaying the scaled complete ultrasound image.

21. The ultrasound scanning system of claim 18 wherein the vertical dimension is less than or equal to the first threshold dimension: comparing, by the processor, the vertical dimension to a second threshold dimension different from the first threshold dimension; when the vertical dimension is less than or equal to the second threshold dimension, displaying the cropped ultrasound image on the application window scaled so that a full height of the cropped ultrasound image corresponds to the vertical dimension and at least one side edge of the complete ultrasound image is not displayed; and when the vertical dimension is greater than the second threshold dimension, scaling the displayed ultrasound image so that the full height of the displayed ultrasound image corresponds to the second threshold dimension.

* * * * *